United States Patent
Sinicropi et al.

(10) Patent No.: US 11,149,297 B2
(45) Date of Patent: *Oct. 19, 2021

(54) METHODS FOR DEPLETING RNA FROM NUCLEIC ACID SAMPLES

(71) Applicant: Genomic Health, Inc., Redwood City, CA (US)

(72) Inventors: Dominick Sinicropi, Woodside, CA (US); John Morlan, Foster City, CA (US)

(73) Assignee: Genomic Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,840

(22) Filed: Jan. 10, 2018

(65) Prior Publication Data
US 2018/0208968 A1   Jul. 26, 2018

Related U.S. Application Data

(62) Division of application No. 14/644,455, filed on Mar. 11, 2015, now Pat. No. 9,902,991, which is a division of application No. 12/940,981, filed on Nov. 5, 2010, now Pat. No. 9,005,891.

(60) Provisional application No. 61/259,934, filed on Nov. 10, 2009.

(51) Int. Cl.
*C12Q 1/68* (2018.01)
*C12Q 1/6806* (2018.01)
*C12Q 1/6848* (2018.01)
*C12N 15/10* (2006.01)

(52) U.S. Cl.
CPC ....... *C12Q 1/6806* (2013.01); *C12N 15/1003* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 6,352,827 B1 | 3/2002 | Lin et al. | |
| 6,613,516 B1* | 9/2003 | Christians | C12N 15/1006 435/194 |
| 7,354,716 B2 | 4/2008 | Huang | |
| 8,076,064 B2 | 12/2011 | Wang | |
| 9,005,891 B2* | 4/2015 | Sinicropi | C12N 15/1003 435/6.1 |
| 9,745,570 B2* | 8/2017 | Sooknanan | C12N 15/1006 |
| 2003/0175709 A1 | 9/2003 | Murphy et al. | |
| 2004/0081969 A1 | 4/2004 | Ilsley | |
| 2005/0003369 A1* | 1/2005 | Christians | C12Q 1/6844 435/6.16 |

(Continued)

OTHER PUBLICATIONS

Invitrogen, RiboMinus Transcriptome Isolation Kit (Version B, Jan. 3, 2005).

*Primary Examiner* — Jeanine A Goldberg
(74) *Attorney, Agent, or Firm* — McNeill Baur PLLC

(57) ABSTRACT

The invention relates to methods of depleting RNA from a nucleic acid sample. The RNA may be any RNA, including, but not limited to, rRNA, tRNA, and mRNA. The method is useful for depleting RNA from a nucleic acid sample obtained from a fixed paraffin-embedded tissue (FPET) sample. The method may also be used to prepare cDNA, in particular, a cDNA library for further analysis or manipulation.

19 Claims, 14 Drawing Sheets

Specification includes a Sequence Listing.

(56) References Cited

U.S. PATENT DOCUMENTS

| | | |
|---|---|---|
| 2005/0196782 A1 | 9/2005 | Keifer et al. |
| 2007/0009913 A1 | 1/2007 | Wang |
| 2007/0009915 A1 | 1/2007 | Wang |
| 2007/0026411 A1 | 2/2007 | Wang et al. |
| 2008/0102454 A1* | 5/2008 | Wang .................. C12Q 1/6806 435/6.18 |
| 2008/0124713 A1 | 5/2008 | Wang |
| 2011/0053150 A1 | 3/2011 | Shirai |

* cited by examiner

SEQUENCE LISTING

<160> NUMBER OF SEQ ID NOS: 91

<210> SEQ ID NO 1
<211> LENGTH: 80
<212> TYPE: DNA
<213> ORGANISM: Artificial Sequence
<220> FEATURE:
<223> OTHER INFORMATION: Synthetic DNA

<400> SEQUENCE: 1

```
ttaatcatgg cctcagttcc gaaaaccaac aaaatagaac cgcggtccta ttccattatt    60
cctagctgcg gtatccaggc                                                80

<210> SEQ ID NO 2
<211> LENGTH: 80
<212> TYPE: DNA
<213> ORGANISM: Artificial Sequence
<220> FEATURE:
<223> OTHER INFORMATION: Synthetic DNA

<400> SEQUENCE: 2
gctttcgctc tggtccgtct tgcgccggtc caagaatttc acctctagcg gcgcaatacg    60
aatgcccccg gccgtccctc                                                80

<210> SEQ ID NO 3
<211> LENGTH: 80
<212> TYPE: DNA
<213> ORGANISM: Artificial Sequence
<220> FEATURE:
<223> OTHER INFORMATION: Synthetic DNA

<400> SEQUENCE: 3
tggtcggaac tacgacggta tctgatcgtc ttcgaacctc cgactttcgt tcttgattaa    60
tgaaaacatt cttggcaaat                                                80

<210> SEQ ID NO 4
<211> LENGTH: 80
<212> TYPE: DNA
<213> ORGANISM: Artificial Sequence
<220> FEATURE:
<223> OTHER INFORMATION: Synthetic DNA

<400> SEQUENCE: 4
tcctcgttca tggggaataa ttgcaatccc cgatccccat cacgaatggg gttcaacggg    60
ttacccgcgc ctgccggcgt                                                80

<210> SEQ ID NO 5
<211> LENGTH: 80
<212> TYPE: DNA
<213> ORGANISM: Artificial Sequence
<220> FEATURE:
<223> OTHER INFORMATION: Synthetic DNA

<400> SEQUENCE: 5
atcggtagta gcgacgggcg gtgtgtacaa agggcaggga cttaatcaac gcaagcttat    60
gacccgcact tactgggaat                                                80

<210> SEQ ID NO 6
<211> LENGTH: 80
<212> TYPE: DNA
<213> ORGANISM: Artificial Sequence
<220> FEATURE:
<223> OTHER INFORMATION: Synthetic DNA

<400> SEQUENCE: 6
ttcgaccgtc ttctcagcgc tccgccaggc cgtgggccga ccccggcggg gccgatccga    60
gggcctcact aaaccatcca                                                80

<210> SEQ ID NO 7
<211> LENGTH: 56
<212> TYPE: DNA
```

```
<213> ORGANISM: Artificial Sequence
<220> FEATURE:
<223> OTHER INFORMATION: Synthetic DNA

<400> SEQUENCE: 7
gggggctcga ggacgggccc ggcgccccgc aagcgaggag gacgacggac ggacgg          56

<210> SEQ ID NO 8
<211> LENGTH: 80
<212> TYPE: DNA
<213> ORGANISM: Artificial Sequence
<220> FEATURE:
<223> OTHER INFORMATION: Synthetic DNA

<400> SEQUENCE: 8
tttgagacaa gcatatgcta ctggcaggat caaccaggta ggtaggtaga gcgcggcgag      60
gccccgacgc ggccggacgg                                                  80

<210> SEQ ID NO 9
<211> LENGTH: 80
<212> TYPE: DNA
<213> ORGANISM: Artificial Sequence
<220> FEATURE:
<223> OTHER INFORMATION: Synthetic DNA

<400> SEQUENCE: 9
aaggaaccat aactgattta atgagccatt cgcagtttca ctgtaccggc cgtgcgtact      60
tagacatgca tggcttaatc                                                  80

<210> SEQ ID NO 10
<211> LENGTH: 80
<212> TYPE: DNA
<213> ORGANISM: Artificial Sequence
<220> FEATURE:
<223> OTHER INFORMATION: Synthetic DNA

<400> SEQUENCE: 10 cgaaggggt cagcgcccgt cggcatgtat tagctctaga attaccacag ttatccaagt       60
aggagaggag cgagcgacca                                                  80

<210> SEQ ID NO 11
<211> LENGTH: 80
<212> TYPE: DNA
<213> ORGANISM: Artificial Sequence
<220> FEATURE:
<223> OTHER INFORMATION: Synthetic DNA

<400> SEQUENCE: 11
ccgcggcccg ccccccggcc ggggccggag agggctgac cgggttggtt ttgatctgat       60
aaatgcacgc atccccccg                                                   80

<210> SEQ ID NO 12
<211> LENGTH: 80
<212> TYPE: DNA
<213> ORGANISM: Artificial Sequence
<220> FEATURE:
<223> OTHER INFORMATION: Synthetic DNA

<400> SEQUENCE: 12
tagggcagac gttcgaatgg gtcgtcgccg ccacgggggg cgtgcgatcg gcccgaggtt      60
atctagagtc accaaagccg                                                  80
```

```
<210> SEQ ID NO 13
<211> LENGTH: 80
<212> TYPE: DNA
<213> ORGANISM: Artificial Sequence
<220> FEATURE:
<223> OTHER INFORMATION: Synthetic DNA

<400> SEQUENCE: 13
ctccctctcc ggaatcgaac cctgattccc cgtcacccgt ggtcaccatg gtaggcacgg      60
cgactaccat cgaaagttga                                                 80

<210> SEQ ID NO 14
<211> LENGTH: 80
<212> TYPE: DNA
<213> ORGANISM: Artificial Sequence
<220> FEATURE:
<223> OTHER INFORMATION: Synthetic DNA

<400> SEQUENCE: 14
ttcgtcacta cctccccggg tcgggagtgg gtaatttgcg cgcctgctgc cttccttgga      60
tgtggtagcc gtttctcagg                                                 80

<210> SEQ ID NO 15
<211> LENGTH: 80
<212> TYPE: DNA
<213> ORGANISM: Artificial Sequence
<220> FEATURE:
<223> OTHER INFORMATION: Synthetic DNA

<400> SEQUENCE: 15
ctccaatgga tcctcgttaa aggatttaaa gtggactcat tccaattaca gggcctcgaa      60
agagtcctgt attgttattt                                                 80

<210> SEQ ID NO 16
<211> LENGTH: 80
<212> TYPE: DNA
<213> ORGANISM: Artificial Sequence
<220> FEATURE:
<223> OTHER INFORMATION: Synthetic DNA

<400> SEQUENCE: 16
ctacgagctt tttaactgca gcaactttaa tatacgctat tggagctgga attaccgcgg      60
ctgctggcac cagacttgcc                                                 80

<210> SEQ ID NO 17
<211> LENGTH: 80
<212> TYPE: DNA
<213> ORGANISM: Artificial Sequence
<220> FEATURE:
<223> OTHER INFORMATION: Synthetic DNA

<400> SEQUENCE: 17 aggggcgcc gagaggcaag gggcggggac gggcggtggc tcgcctcgcg gcggaccgcc      60
cgcccgctcc caagatccaa                                                 80

<210> SEQ ID NO 18
<211> LENGTH: 80
<212> TYPE: DNA
<213> ORGANISM: Artificial Sequence
<220> FEATURE:
<223> OTHER INFORMATION: Synthetic DNA

<400> SEQUENCE: 18
```

```
ggctcgggcc tgctttgaac actctaattt tttcaaagta aacgcttcgg gccccgcggg    60
acactcagct aagagcatcg                                                80

<210> SEQ ID NO 19
<211> LENGTH: 80
<212> TYPE: DNA
<213> ORGANISM: Artificial Sequence
<220> FEATURE:
<223> OTHER INFORMATION: Synthetic DNA

<400> SEQUENCE: 19
acccaaagac tttggtttcc cggaagctgc ccggcgggtc atgggaataa cgccgccgca    60
tcgccggtcg gcatcgttta                                                80

<210> SEQ ID NO 20
<211> LENGTH: 80
<212> TYPE: DNA
<213> ORGANISM: Artificial Sequence
<220> FEATURE:
<223> OTHER INFORMATION: Synthetic DNA

<400> SEQUENCE: 20
taagccgcag gctccactcc tggtggtgcc cttccgtcaa ttcctttaag tttcagcttt    60
gcaaccatac tcccccgga                                                 80

<210> SEQ ID NO 21
<211> LENGTH: 80
<212> TYPE: DNA
<213> ORGANISM: Artificial Sequence
<220> FEATURE:
<223> OTHER INFORMATION: Synthetic DNA

<400> SEQUENCE: 21
cacggaatcg agaaagagct atcaatctgt caatcctgtc cgtgtccggg ccgggtgagg    60
tttcccgtgt tgagtcaaat                                                80

<210> SEQ ID NO 22
<211> LENGTH: 80
<212> TYPE: DNA
<213> ORGANISM: Artificial Sequence
<220> FEATURE:
<223> OTHER INFORMATION: Synthetic DNA

<400> SEQUENCE: 22
agcatgccag agtctcgttc gttatcggaa ttaaccagac aaatcgctcc accaactaag    60
aacggccatg caccaccacc                                                80

<210> SEQ ID NO 23
<211> LENGTH: 80
<212> TYPE: DNA
<213> ORGANISM: Artificial Sequence
<220> FEATURE:
<223> OTHER INFORMATION: Synthetic DNA

<400> SEQUENCE: 23
tcaatctcgg gtggctgaac gccacttgtc cctctaagaa gttggggac gccgaccgct    60 cggggtcgc gtaactagtt                                                 80

<210> SEQ ID NO 24
<211> LENGTH: 80
<212> TYPE: DNA
<213> ORGANISM: Artificial Sequence
```

<220> FEATURE:
<223> OTHER INFORMATION: Synthetic DNA

<400> SEQUENCE: 24
agggtaggca cacgctgagc cagtcagtgt agcgcgcgtg cagccccgga catctaaggg    60
catcacagac ctgttattgc    80

<210> SEQ ID NO 25
<211> LENGTH: 68
<212> TYPE: DNA
<213> ORGANISM: Artificial Sequence
<220> FEATURE:
<223> OTHER INFORMATION: Synthetic DNA

<400> SEQUENCE: 25
taatgatcct tccgcaggtt cacctacgga aaccttgtta cgactttttac ttcctctaga    60 tagtcaag    68

<210> SEQ ID NO 26
<211> LENGTH: 80
<212> TYPE: DNA
<213> ORGANISM: Artificial Sequence
<220> FEATURE:
<223> OTHER INFORMATION: Synthetic DNA

<400> SEQUENCE: 26
ggaatcctgg ttagtttctt ttcctccgct gactaatatg cttaaattca gcgggtcgcc    60
acgtctgatc tgaggtcgcg    80

<210> SEQ ID NO 27
<211> LENGTH: 80
<212> TYPE: DNA
<213> ORGANISM: Artificial Sequence
<220> FEATURE:
<223> OTHER INFORMATION: Synthetic DNA

<400> SEQUENCE: 27
ttccgtacgc cacatgtccc gcgccccgcg gggcggggat tcggcgctgg gctcttccct    60
gttcactcgc cgttactgag    80

<210> SEQ ID NO 28
<211> LENGTH: 80
<212> TYPE: DNA
<213> ORGANISM: Artificial Sequence
<220> FEATURE:
<223> OTHER INFORMATION: Synthetic DNA

<400> SEQUENCE: 28
taccggcctc acaccgtcca cgggctgggc ctcgatcaga aggacttggg ccccccacga    60
gcggcgccgg ggagcgggtc    80

<210> SEQ ID NO 29
<211> LENGTH: 80
<212> TYPE: DNA
<213> ORGANISM: Artificial Seqence
<220> FEATURE:
<223> OTHER INFORMATION: Synthetic DNA

<400> SEQUENCE: 29
ttagatggag tttaccaccc gctttgggct gcattcccaa gcaacccgac tccgggaaga    60
cccgggcgcg cgccggccgc    80

<210> SEQ ID NO 30
<211> LENGTH: 80
<212> TYPE: DNA
<213> ORGANISM: Artificial Sequences
<220> FEATURE:
<223> OTHER INFORMATION: Synthetic DNA

<400> SEQUENCE: 30
cttgaactct ctcttcaaag ttcttttcaa ctttcccttn cggtacttgt tgactatcgg    60
tctcgtgccg gtatttagcc                                                80

<210> SEQ ID NO 31
<211> LENGTH: 80
<212> TYPE: DNA
<213> ORGANISM: Artificial Sequence
<220> FEATURE:
<223> OTHER INFORMATION: Synthetic DNA

<400> SEQUENCE: 31
gccggacccg ccgccgggtt gaatcctccg ggcggactgc gcggaccccca cccgtttacc    60 tcttaacggt ttcacgccct                                                80

<210> SEQ ID NO 32
<211> LENGTH: 80
<212> TYPE: DNA
<213> ORGANISM: Artificial Sequence
<220> FEATURE:
<223> OTHER INFORMATION: Synthetic DNA

<400> SEQUENCE: 32
ggggcggcgg gggaagggag ggcgggtgga ggggtcggga ggaacggggg gcgggaaaga    60
tccgccgggc cgccgacacg                                                80

<210> SEQ ID NO 33
<211> LENGTH: 80
<212> TYPE: DNA
<213> ORGANISM: Artificial Sequence
<220> FEATURE:
<223> OTHER INFORMATION: Synthetic DNA

<400> SEQUENCE: 33 tccccgccg accccacccc cggccccgcc cgcccacccc cgcacccgcc ggagcccgcc    60
ccctccgggg aggaggagga                                                80

<210> SEQ ID NO 34
<211> LENGTH: 80
<212> TYPE: DNA
<213> ORGANISM: Artificial Sequence
<220> FEATURE:
<223> OTHER INFORMATION: Synthetic DNA

<400> SEQUENCE: 34
tcccagccgt cccggagccg gtcgcggcgc accgcctgga aatgcgcccg gcggcggccg    60
gtcgccggtc cggggacgg                                                 80

<210> SEQ ID NO 35
<211> LENGTH: 80
<212> TYPE: DNA
<213> ORGANISM: Artificial Sequence
<220> FEATURE:
<223> OTHER INFORMATION: Synthetic DNA

<400> SEQUENCE: 35

```
ggggccgggg ggcggagacg ggggaggagg aggacggacg gacggacggg gcccccccgag    60 ccaccttccc cgccgggcct                                                  80

<210> SEQ ID NO 36
<211> LENGTH: 80
<212> TYPE: DNA
<213> ORGANISM: Artificial Sequence
<220> FEATURE:
<223> OTHER INFORMATION: Synthetic DNA

<400> SEQUENCE: 36
cggtcccgcc gcccccgccg ccgccgccac cgccgccgcc ccgccgcccc cgacccgcgc    60
gccctcccga gggaggacgc                                                  80

<210> SEQ ID NO 37
<211> LENGTH: 80
<212> TYPE: DNA
<213> ORGANISM: Artificial Sequence
<220> FEATURE:
<223> OTHER INFORMATION: Synthetic DNA

<400> SEQUENCE: 37
cggcgacggg tctcgctccc tcggccccgg gattcggcga gtgctgctgc cggggggggct    60 gtaacactcg ggggggggttt                                                 80

<210> SEQ ID NO 38
<211> LENGTH: 80
<212> TYPE: DNA
<213> ORGANISM: Artificial Sequence
<220> FEATURE:
<223> OTHER INFORMATION: Synthetic DNA

<400> SEQUENCE: 38
aggagacgcc ggcgccgcgc cgggggagac cccctcgcg gggattcccg cgggggtggg    60
cgccgggagg ggggagagcg                                                  80

<210> SEQ ID NO 39
<211> LENGTH: 80
<212> TYPE: DNA
<213> ORGANISM: Artificial Sequence
<220> FEATURE:
<223> OTHER INFORMATION: Synthetic DNA

<400> SEQUENCE: 39
cccgtcgccg gggcgggggc gcggggagga ggggtgggag agcggtcgcg ccgtgggagg    60
ggtggcccgg ccccccccacg                                                 80

<210> SEQ ID NO 40
<211> LENGTH: 80
<212> TYPE: DNA
<213> ORGANISM: Artificial Sequence
<220> FEATURE:
<223> OTHER INFORMATION: Synthetic DNA

<400> SEQUENCE: 40
ccccgggccc gacggcgcga cccgcccggg gcgcactggg gacagtccgc cccgcccccc    60
gacccgcgcg cggcaccccc                                                  80

<210> SEQ ID NO 41
<211> LENGTH: 80
<212> TYPE: DNA
```

<213> ORGANISM: Artificial Sequence
<220> FEATURE:
<223> OTHER INFORMATION: Synthetic DNA

<400> SEQUENCE: 41
ccgacgtcgc cgccgacccc gtgcgctcgc tccgccgtcc ccctcttcgg gggacgcgcg    60
cgtggccccg agagaacctc                                                80

<210> SEQ ID NO 42
<211> LENGTH: 80
<212> TYPE: DNA
<213> ORGANISM: Artificial Sequence
<220> FEATURE:
<223> OTHER INFORMATION: Synthetic DNA

<400> SEQUENCE: 42
cggcggcttt cgtgcgagcc cccgactcgc gcacgtgtta gactccttgg tccgtgtttc    60
aagacgggtc gggtgggtag                                                80

<210> SEQ ID NO 43
<211> LENGTH: 80
<212> TYPE: DNA
<213> ORGANISM: Artificial Sequence
<220> FEATURE:
<223> OTHER INFORMATION: Synthetic DNA

<400> SEQUENCE: 43
ggtgcccctc ggcggactgg agaggcctcg ggatcccacc tcggccggcg agcgcgccgg    60
ccttcacctt cattgcgcca                                                80

<210> SEQ ID NO 44
<211> LENGTH: 80
<212> TYPE: DNA
<213> ORGANISM: Artificial Sequence
<220> FEATURE:
<223> OTHER INFORMATION: Synthetic DNA

<400> SEQUENCE: 44
ggcatagttc accatctttc gggtcctaac acgtgcgctc gtgctccacc tccccggcgc    60
ggcgggcgag acgggccggt                                                80

<210> SEQ ID NO 45
<211> LENGTH: 80
<212> TYPE: DNA
<213> ORGANISM: Artificial Sequence
<220> FEATURE:
<223> OTHER INFORMATION: Synthetic DNA

<400> SEQUENCE: 45
tacccaggtc ggacgaccga tttgcacgtc aggaccgcta cggacctcca ccagagtttc    60
ctctggcttc gccctgccca                                                80

<210> SEQ ID NO 46
<211> LENGTH: 80
<212> TYPE: DNA
<213> ORGANISM: Artificial Sequence
<220> FEATURE:
<223> OTHER INFORMATION: Synthetic DNA

<400> SEQUENCE: 46
tctgcgagag cgccagctat cctgagggaa acttcggagg gaaccagcta ctagatggtt    60
cgattagtct ttcgccccta                                                80

<210> SEQ ID NO 47
<211> LENGTH: 80
<212> TYPE: DNA
<213> ORGANISM: Artificial Sequence
<220> FEATURE:
<223> OTHER INFORMATION: Synthetic DNA

<400> SEQUENCE: 47
ataggttgag atcgtttcgg ccccaagacc tctaatcatt cgctttaccg gataaaactg    60
cgtggcgggg gtgcgtcggg                                                80

<210> SEQ ID NO 48
<211> LENGTH: 80
<212> TYPE: DNA
<213> ORGANISM: Artificial Sequence
<220> FEATURE:
<223> OTHER INFORMATION: Synthetic DNA

<400> SEQUENCE: 48
aaagtggccc actaggcact cgcattccac cccggctcca cgccagcgag ccgggcttct    60
tacccattta aagtttgaga                                                80

<210> SEQ ID NO 49
<211> LENGTH: 80
<212> TYPE: DNA
<213> ORGANISM: Artificial Sequence
<220> FEATURE:
<223> OTHER INFORMATION: Synthetic DNA

<400> SEQUENCE: 49
ttctggggtc tgatgagcgt cggcatcggg cgccttaacc cggcgttcgg ttcatcccgc    60
agcgccagtt ctgcttacca                                                80

<210> SEQ ID NO 50
<211> LENGTH: 80
<212> TYPE: DNA
<213> ORGANISM: Artificial Sequence
<220> FEATURE:
<223> OTHER INFORMATION: Synthetic DNA

<400> SEQUENCE: 50
gcaggtgagt tgttacacac tccttagcgg attccgactt ccatggccac cgtcctgctg    60
tctatatcaa ccaacacctt                                                80

<210> SEQ ID NO 51
<211> LENGTH: 80
<212> TYPE: DNA
<213> ORGANISM: Artificial Sequence
<220> FEATURE:
<223> OTHER INFORMATION: Synthetic DNA

<400> SEQUENCE: 51
cgtccactct cgactgccgg cgacggccgg gtatgggccc gacgctccag cgccatccat    60
tttcagggct agttgattcg                                                80

<210> SEQ ID NO 52
<211> LENGTH: 80
<212> TYPE: DNA
<213> ORGANISM: Artificial Sequence
<220> FEATURE:
<223> OTHER INFORMATION: Synthetic DNA -continued

```
<400> SEQUENCE: 52
cccacacccc cgccgccgcc gccgccgccg ccctccgacg cacaccacac gcgcgcgcgc      60
gccgccgccc ccgccgctcc                                                  80

<210> SEQ ID NO 53
<211> LENGTH: 80
<212> TYPE: DNA
<213> ORGANISM: Artificial Sequence
<220> FEATURE:
<223> OTHER INFORMATION: Synthetic DNA

<400> SEQUENCE: 53
tccgcggggc tccgggggcg gggagcgggg cgtgggcggg aggaggggag gaggcgtggg      60 gggggggggcg ggggaaggac                                                 80

<210> SEQ ID NO 54
<211> LENGTH: 80
<212> TYPE: DNA
<213> ORGANISM: Artificial Sequence
<220> FEATURE:
<223> OTHER INFORMATION: Synthetic DNA

<400> SEQUENCE: 54
cctgcggcgg cctccacccg ggcccgcgcc ctaggcttca aggctcaccg cagcggccct      60
cctactcgtc gcggcgtagc                                                  80

<210> SEQ ID NO 55
<211> LENGTH: 80
<212> TYPE: DNA
<213> ORGANISM: Artificial Sequence
<220> FEATURE:
<223> OTHER INFORMATION: Synthetic DNA

<400> SEQUENCE: 55
tgctgttcac atggaaccct tctccacttc ggccttcaaa gttctcgttt gaatatttgc      60
tactaccacc aagatctgca                                                  80

<210> SEQ ID NO 56
<211> LENGTH: 80
<212> TYPE: DNA
<213> ORGANISM: Artificial Sequence
<220> FEATURE:
<223> OTHER INFORMATION: Synthetic DNA

<400> SEQUENCE: 56
ccgagggcaa cggaggccat cgcccgtccc ttcggaacgg cgctcgccca tctctcagga      60
ccgactgacc catgttcaac                                                  80

<210> SEQ ID NO 57
<211> LENGTH: 80
<212> TYPE: DNA
<213> ORGANISM: Artificial Sequence
<220> FEATURE:
<223> OTHER INFORMATION: Synthetic DNA

<400> SEQUENCE: 57
gttaccgcac tggacgcctc gcggcgccca tctccgccac tccggattcg gggatctgaa      60
cccgactccc tttcgatcgg                                                  80

<210> SEQ ID NO 58
<211> LENGTH: 80
```

```
<212> TYPE: DNA
<213> ORGANISM: Artificial Sequence
<220> FEATURE:
<223> OTHER INFORMATION: Synthetic DNA

<400> SEQUENCE: 58
ccattccagg gcgccctgcc cttcacaaag aaaagagaac tctccccggg gctcccgccg      60
gcttctccgg gatcggtcgc                                                  80

<210> SEQ ID NO 59
<211> LENGTH: 80
<212> TYPE: DNA
<213> ORGANISM: Artificial Sequence
<220> FEATURE:
<223> OTHER INFORMATION: Synthetic DNA

<400> SEQUENCE: 59
tcaagggcca gcgagagctc accggacgcc gccggaaccg cgacgctttc caaggcacgg      60 gccctctct cggggcgaac                                                   80

<210> SEQ ID NO 60
<211> LENGTH: 80
<212> TYPE: DNA
<213> ORGANISM: Artificial Sequence
<220> FEATURE:
<223> OTHER INFORMATION: Synthetic DNA

<400> SEQUENCE: 60
ccagaggctg ttcaccttgg agacctgctg cggatatggg tacggcccgg cgcgagattt      60
acaccctctc ccccggattt                                                  80

<210> SEQ ID NO 61
<211> LENGTH: 80
<212> TYPE: DNA
<213> ORGANISM: Artificial Sequence
<220> FEATURE:
<223> OTHER INFORMATION: Synthetic DNA

<400> SEQUENCE: 61
cccagcccct agagccaatc cttatcccga agttacggat ccggcttgcc gacttccctt      60
acctacattg ttccaacatg                                                  80

<210> SEQ ID NO 62
<211> LENGTH: 80
<212> TYPE: DNA
<213> ORGANISM: Artificial Sequence
<220> FEATURE:
<223> OTHER INFORMATION: Synthetic DNA

<400> SEQUENCE: 62
tgccccgggc gtgggggggg cgcgcgcctc gtccagccgc ggcgcgcgcc cagccccgct      60
tcgcgcccca gcccgaccga                                                  80

<210> SEQ ID NO 63
<211> LENGTH: 80
<212> TYPE: DNA
<213> ORGANISM: Artificial Sequence
<220> FEATURE:
<223> OTHER INFORMATION: Synthetic DNA

<400> SEQUENCE: 63
agagagagag agagagggcg cggggtgggg agggagcgag cggcgcgcgc gggtggggcg      60
```

```
ggggagggcc gcgagggggg                                              80

<210> SEQ ID NO 64
<211> LENGTH: 80
<212> TYPE: DNA
<213> ORGANISM: Artificial Sequence
<220> FEATURE:
<223> OTHER INFORMATION: Synthetic DNA

<400> SEQUENCE: 64
cctgccgccc cgaccettct ccccccgccg cgccccacg cggcgctccc ccggggaggg    60
gggaggacgg ggagcggggg                                              80

<210> SEQ ID NO 65
<211> LENGTH: 80
<212> TYPE: DNA
<213> ORGANISM: Artificial Sequence
<220> FEATURE:
<223> OTHER INFORMATION: Synthetic DNA

<400> SEQUENCE: 65
gccgccggcc ccccgggtcc ccggggcccc cctcgcgggg acctgccccc gccggccgcc    60
ccggcggccg ccgcgcggcc                                              80

<210> SEQ ID NO 66
<211> LENGTH: 80
<212> TYPE: DNA
<213> ORGANISM: Artificial Sequence
<220> FEATURE:
<223> OTHER INFORMATION: Synthetic DNA

<400> SEQUENCE: 66
ctccccgggg gcggccgcga cgcccgccgc agctggggcg atccacggga agggcccggc    60
tcgcgtccag agtccgcgcc                                              80

<210> SEQ ID NO 67
<211> LENGTH: 80
<212> TYPE: DNA
<213> ORGANISM: Artificial Sequence
<220> FEATURE:
<223> OTHER INFORMATION: Synthetic DNA

<400> SEQUENCE: 67
cgaccgctcc cgcccccagc ggacgcgcgc gcgaccgaga cgtggggtgg gggtgggggg    60
cgcgccgcgc cgccgccggg                                              80

<210> SEQ ID NO 68
<211> LENGTH: 80
<212> TYPE: DNA
<213> ORGANISM: Artificial Sequence
<220> FEATURE:
<223> OTHER INFORMATION: Synthetic DNA

<400> SEQUENCE: 68
gaacgggggg cggacggggc cgggggggta gggcggggggg acgaaccgcc ccgccccgcc    60
gcccgccgac cgccgccgcc                                              80

<210> SEQ ID NO 69
<211> LENGTH: 80
<212> TYPE: DNA
<213> ORGANISM: Artificial Sequence
<220> FEATURE:
<223> OTHER INFORMATION: Synthetic DNA
```

<400> SEQUENCE: 69
ggcggacccg gcggggggga ccggcccgcg gcccctccgc cgcctgccgc cgccgccgcc    60
gcgcgccgag gaggaggggg                                                80

<210> SEQ ID NO 70
<211> LENGTH: 80
<212> TYPE: DNA
<213> ORGANISM: Artificial Sequence
<220> FEATURE:
<223> OTHER INFORMATION: Synthetic DNA

<400> SEQUENCE: 70 attccccctgg tccgcaccag ttctaagtcg gctgctaggc gccggccgag gcgaggcgcg    60
cgcggaaccg cggcccccggg                                               80

<210> SEQ ID NO 71
<211> LENGTH: 80
<212> TYPE: DNA
<213> ORGANISM: Artificial Sequence
<220> FEATURE:
<223> OTHER INFORMATION: Synthetic DNA

<400> SEQUENCE: 71
tcagagcact gggcagaaat cacatcgcgt caacacccgc cgcgggcctt cgcgatgctt    60
tgttttaatt aaacagtcgg                                                80

<210> SEQ ID NO 72
<211> LENGTH: 80
<212> TYPE: DNA
<213> ORGANISM: Artificial Sequence
<220> FEATURE:
<223> OTHER INFORMATION: Synthetic DNA

<400> SEQUENCE: 72
gaggcatttg gctaccttaa gagagtcata gttactcccg ccgtttaccc gcgcttcatt    60
gaatttcttc actttgacat                                                80

<210> SEQ ID NO 73
<211> LENGTH: 80
<212> TYPE: DNA
<213> ORGANISM: Artificial Sequence
<220> FEATURE:
<223> OTHER INFORMATION: Synthetic DNA

<400> SEQUENCE: 73
tggctgtggt ttcgctggat agtaggtagg gacagtggga atctcgttca tccattcatg    60
cgcgtcacta attagatgac                                                80

<210> SEQ ID NO 74
<211> LENGTH: 80
<212> TYPE: DNA
<213> ORGANISM: Artificial Sequence
<220> FEATURE:
<223> OTHER INFORMATION: Synthetic DNA

<400> SEQUENCE: 74
catgtctctt caccgtgcca gactagagtc aagctcaaca gggtcttctt tccccgctga    60
ttccgccaag cccgttccct                                                80

<210> SEQ ID NO 75

```
<211> LENGTH: 80
<212> TYPE: DNA
<213> ORGANISM: Artificial Sequence
<220> FEATURE:
<223> OTHER INFORMATION: Synthetic DNA

<400> SEQUENCE: 75
cagggccgcg accccgccc cgggcccctc gcggggacac cggggggcg ccggggcct      60 cccacttatt ctacacctct                                                80

<210> SEQ ID NO 76
<211> LENGTH: 80
<212> TYPE: DNA
<213> ORGANISM: Artificial Sequence
<220> FEATURE:
<223> OTHER INFORMATION: Synthetic DNA

<400> SEQUENCE: 76
agagcccctc gggctcgccc ccccgcctca ccgggtcagt gaaaaaacga tcagagtagt    60
ggtatttcac cggcggcccg                                                80

<210> SEQ ID NO 77
<211> LENGTH: 80
<212> TYPE: DNA
<213> ORGANISM: Artificial Sequence
<220> FEATURE:
<223> OTHER INFORMATION: Synthetic DNA

<400> SEQUENCE: 77
cgccccagtc aaactcccca cctggcactg tccccggagc gggtcgcgcc cggccgggcg    60
ggcgcttggc gccagaagcg                                                80

<210> SEQ ID NO 78
<211> LENGTH: 80
<212> TYPE: DNA
<213> ORGANISM: Artificial Sequence
<220> FEATURE:
<223> OTHER INFORMATION: Synthetic DNA

<400> SEQUENCE: 78
ttgcccttct gctccacggg aggtttctgt cctccctgag ctcgccttag acacctgcg     60 ttaccgtttg acaggtgtac                                                80

<210> SEQ ID NO 79
<211> LENGTH: 80
<212> TYPE: DNA
<213> ORGANISM: Artificial Sequence
<220> FEATURE:
<223> OTHER INFORMATION: Synthetic DNA

<400> SEQUENCE: 79
aaacccaaaa ggtcagaagg atcgtgaggc cccgctttca cggtctgtat tcgtactgaa    60
aatcaagatc aagcgagctt                                                80

<210> SEQ ID NO 80
<211> LENGTH: 80
<212> TYPE: DNA
<213> ORGANISM: Artificial Sequence
<220> FEATURE:
<223> OTHER INFORMATION: Synthetic DNA

<400> SEQUENCE: 80
caaaaagcga cgtcgctatg aacgcttggc cgccacaagc cagttatccc tgtggtaact    60
```
tttctgacac ctcctgctta                                                        80

<210> SEQ ID NO 81
<211> LENGTH: 80
<212> TYPE: DNA
<213> ORGANISM: Artificial Sequence
<220> FEATURE:
<223> OTHER INFORMATION: Synthetic DNA

<400> SEQUENCE: 81
cgttccctat tagtgggtga acaatccaac gcttggcgaa ttctgcttca caatgatagg          60
aagagccgac atcgaaggat                                                        80

<210> SEQ ID NO 82
<211> LENGTH: 80
<212> TYPE: DNA
<213> ORGANISM: Artificial Sequence
<220> FEATURE:
<223> OTHER INFORMATION: Synthetic DNA

<400> SEQUENCE: 82
ctgagcagga ttaccatggc aacaacacat catcagtagg gtaaaactaa cctgtctcac          60
gacggtctaa acccagctca                                                        80

<210> SEQ ID NO 83
<211> LENGTH: 80
<212> TYPE: DNA
<213> ORGANISM: Artificial Sequence
<220> FEATURE:
<223> OTHER INFORMATION: Synthetic DNA

<400> SEQUENCE: 83
cccacagatg gtagcttcgc cccattggct cctcagccaa gcacatacac caaatgtctg          60
aacctgcggt tcctctcgta                                                        80

<210> SEQ ID NO 84
<211> LENGTH: 80
<212> TYPE: DNA
<213> ORGANISM: Artificial Sequence
<220> FEATURE:
<223> OTHER INFORMATION: Synthetic DNA

<400> SEQUENCE: 84
ccgaggccaa ccgaggctcc gcggcgctgc cgtatcgttc gcctgggcgg gattctgact          60
tagaggcgtt cagtcataat                                                        80

<210> SEQ ID NO 85
<211> LENGTH: 80
<212> TYPE: DNA
<213> ORGANISM: Artificial Sequence
<220> FEATURE:
<223> OTHER INFORMATION: Synthetic DNA

<400> SEQUENCE: 85
gcggggcacg cgccctcccg cggcggggcg cgtggagggg ggggcggccc gccggcgggg          60
acaggcgggg gaccggctat                                                        80

<210> SEQ ID NO 86
<211> LENGTH: 80
<212> TYPE: DNA
<213> ORGANISM: Artificial Sequence
<220> FEATURE:

```
<223> OTHER INFORMATION: Synthetic DNA

<400> SEQUENCE: 86 aggggggcggc cgcctttccg gccgcgcccc gtttcccagg acgaagggca ctccgcaccg    60 gacccggtc ccggcgcgcg                                                  80

<210> SEQ ID NO 87
<211> LENGTH: 80
<212> TYPE: DNA
<213> ORGANISM: Artificial Sequence
<220> FEATURE:
<223> OTHER INFORMATION: Synthetic DNA

<400> SEQUENCE: 87
cgaaaccccg acccagaagc aggtcgtcta cgaatggttt agcgccaggt tccccacgaa    60
cgtgcggtgc gtgacgggcg                                                 80

<210> SEQ ID NO 88
<211> LENGTH: 65
<212> TYPE: DNA
<213> ORGANISM: Artificial Sequence
<220> FEATURE:
<223> OTHER INFORMATION: Synthetic DNA

<400> SEQUENCE: 88
gacaaaccct tgtgtcgagg gctgactttc aatagatcgc agcgagggag ctgctctgct    60
acgta                                                                 65

<210> SEQ ID NO 89
<211> LENGTH: 58
<212> TYPE: DNA
<213> ORGANISM: Artificial Sequence
<220> FEATURE:
<223> OTHER INFORMATION: Synthetic DNA

<400> SEQUENCE: 89
agatcggaag agcgtcgtgt agggaaagag tgtagatctc ggtggtcgcc gtatcatt      58

<210> SEQ ID NO 90
<211> LENGTH: 24
<212> TYPE: DNA
<213> ORGANISM: Artificial Sequence
<220> FEATURE:
<223> OTHER INFORMATION: Synthetic DNA

<400> SEQUENCE: 90
caagcagaag acggcatacg agat                                            24

<210> SEQ ID NO 91
<211> LENGTH: 16
<212> TYPE: DNA
<213> ORGANISM: Artificial Sequence
<220> FEATURE:
<223> OTHER INFORMATION: Synthetic DNA

<400> SEQUENCE: 91
gggagacgcg tgtaaa                                                     16
```

METHODS FOR DEPLETING RNA FROM NUCLEIC ACID SAMPLES

This application is a divisional of U.S. application Ser. No. 14/644,455, filed on Mar. 11, 2015, which is a divisional of U.S. application Ser. No. 12/940,981, filed Nov. 5, 2010, issued on Apr. 14, 2015, as U.S. Pat. No. 9,005,891 B2, which claims priority benefit of U.S. Provisional Application No. 61/259,934, filed on Nov. 10, 2009, the entire disclosures of which are incorporated herein by reference in their entirety.

This application contains a Sequence Listing in an ASCII text file named "GHI041USSeqListing.txt" created Nov. 5, 2010 (24,000 bytes), which is incorporated herein by reference.

FIELD OF THE INVENTION

The present invention relates to methods of depleting undesired RNA from nucleic acid samples. The invention is useful for preparing cDNA from the RNA-depleted nucleic acid samples, for example, from fixed paraffin embedded tissue (FPET) samples.

INTRODUCTION

The most commonly used methods known in the art for the detection and/or quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); microarrays (Schena et al., *Proc. Natl. Acad. Sci. USA* 93(2):106-149 (1996)), and reverse transcription polymerase chain reaction (RT-PCR) (Weis et al., *Trends in Genetics* 8:263-264 (1992)). Alternatively, antibodies may be employed that can recognize specific hybrids, including DNA hybrids, RNA hybrids, and DNA-RNA hybrid hybrids or DNA-protein hybrids. Of these, due to its sensitivity, reproducibility, and large dynamic range, real-time reverse transcription PCR (RT-PCR) is increasingly becoming the method of choice for high-throughput, accurate expression profiling of a large number of genes.

As RNA cannot serve as a template for PCR, the first step in gene expression profiling by RT-PCR is the reverse transcription of the RNA template into cDNA, followed by its exponential amplification in a PCR reaction. The conversion of mRNA to cDNA is typically performed by oligo dT priming, random priming, or gene-specific priming of the mRNA in the presence of the reverse transcriptase (RT) enzyme. However, some samples may contain additional material that may interfere with the detection and/or quantification of the mRNA. For example, fixed, paraffin-embedded tissue samples may be archived for as long as 10-20 years and may be badly degraded. RNA isolated from such samples may be difficult to efficiently convert into cDNA.

SUMMARY

It is often desirable to isolate, enrich, or increase sequences within a much larger population of sequences in order to limit analysis to those sequences of interest and to reduce interference and unnecessary work that may be caused by the presence of undesirable sequences. The disclosed invention provides a novel method that depletes undesired sequences from a sample containing a mixture of sequences and therefore, enriches for a population of interest.

The present invention provides a method of depleting ribonucleic acid (RNA) from a nucleic acid sample. The method comprises contacting the sample with at least one deoxyribonucleic (DNA) probe complementary to a target RNA. In an embodiment of the invention, the sample is contacted with a single DNA probe. In a further embodiment, the sample is contacted with a multiplicity of DNA probes. In another embodiment, the DNA probe(s) specifically hybridizes to substantially the entire full-length sequence or the entire full-length sequence of the target RNA and forms a DNA-RNA hybrid. The sample is then contacted with a nuclease enzyme, for example a a ribonuclease, and the nuclease enzyme degrades the target RNA in the DNA-RNA hybrid. In an embodiment of the invention, the nuclease enzyme is RNase H, for example a thermostable RNase H. Optionally, the sample may be additionally contacted with a deoxyribonuclease (DNase) to degrade the DNA probe. In one embodiment, the DNase is DNase I. In another embodiment of the invention, the target RNA comprises less than 10% of all RNA present in the nucleic acid sample after RNA depletion.

In a further embodiment of the invention, the target RNA is ribosomal RNA (rRNA), transfer RNA (tRNA) and/or messenger RNA (mRNA). The target rRNA may be eukaryotic rRNA. In a specific embodiment of the invention, the target rRNA is the cytoplasmic 28S or 18S rRNA, or both. In another embodiment, the target rRNA is the mitochondrial rRNA 12S or 16S rRNA, or both.

In an embodiment of the invention, the target RNA is mRNA. The target mRNA may include cellular transcripts that are highly expressed. Thus, in an embodiment of the invention, the target mRNA is selected from GAPDH, ACTB, and TUBB.

In yet another embodiment of the invention, the nucleic acid sample comprises total RNA or amplified RNA. In a specific embodiment, the nucleic acid sample is obtained from a fixed paraffin-embedded tissue (FPET) sample. Thus, the method of the invention can be used to deplete RNA from a nucleic acid sample obtained from an FPET sample. The FPET sample may be from a tumor, and the tumor may be a cancer. In an embodiment of the invention, the cancer is selected from breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The method of the present invention can be further used to prepare cDNA useful for further analysis. In this aspect, cDNA is prepared from the nucleic acid sample after RNA depletion. The cDNA may be purified and/or amplified and may be a cDNA library. The cDNA may be used for further analysis, such as sequencing and/or gene expression analysis.

DETAILED DESCRIPTION

Figure 1:
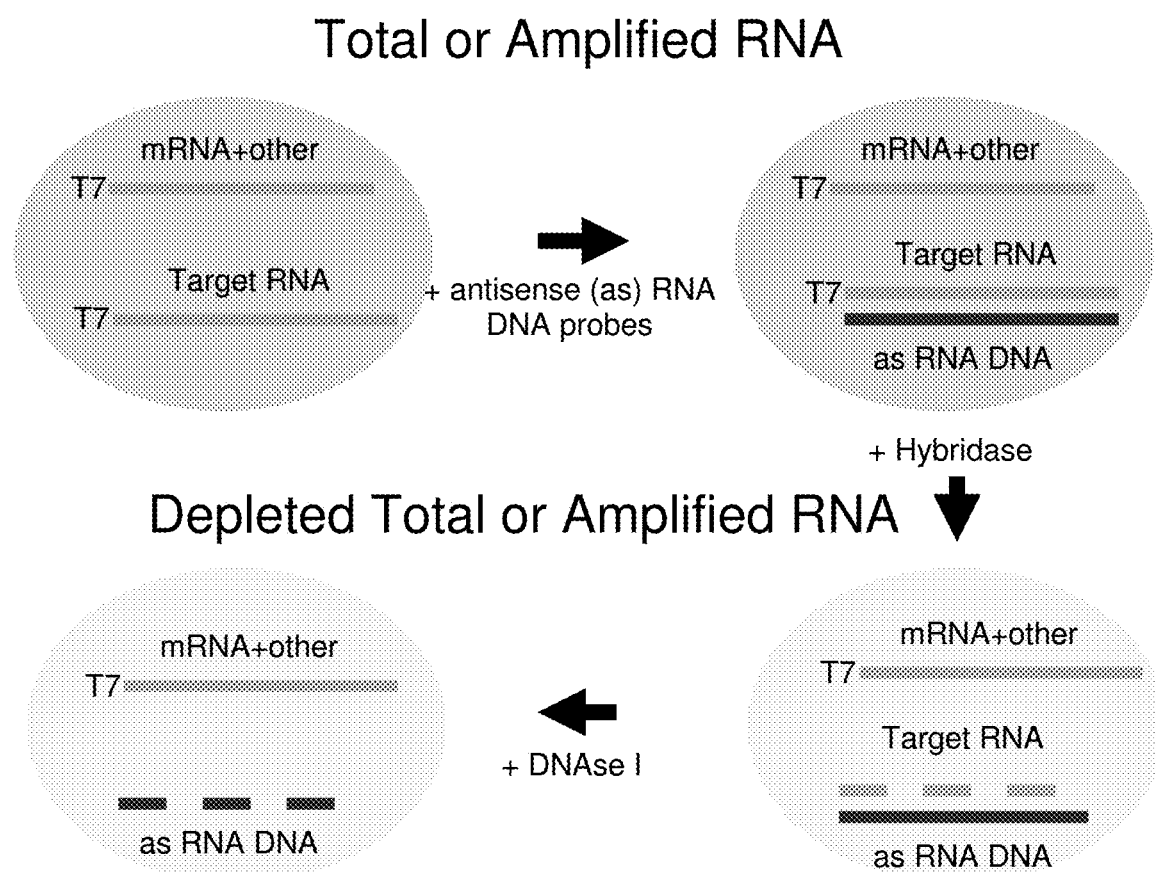
FIG. 1 is a schematic illustration of a method for depleting RNA from a nucleic acid sample comprising total or amplified RNA. When the starting material is amplified RNA and the RNA is amplified as illustrated in FIG. 2 and described below, the resulting RNA comprises a T7 promoter sequence (T7) appended at the end of each strand.

Unless defined otherwise, technical and scientific terms used herein have the same meaning as commonly understood by one of ordinary skill in the art to which this invention belongs. For example, Singleton et al., Dictionary of Microbiology and Molecular Biology 2nd ed., J. Wiley & Sons (New York, N.Y. 1994), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Additionally, the practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

As used herein, the term "nucleic acid" refers to a deoxyribonucleotide or ribonucleotide polymer. The nucleic acid may be unmodified RNA or DNA or modified RNA or DNA and includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In general, the term "nucleic acid" embraces all chemically, enzymatically and/or metabolically modified forms of unmodified nucleic acids, as well as the chemical forms of DNA and RNA characteristic of viruses and cells, including simple and complex cells.

As used herein, the term "nucleic acid sample" refers to a sample containing both desired and undesired nucleic acids. As a non-limiting example, a nucleic acid sample comprises total genomic DNA, total cellular RNA, or a combination thereof. Moreover, a nucleic acid sample may have been enriched for a given population of nucleic acids but includes other undesirable nucleic acids. For example, a nucleic acid sample may be a sample that has been enriched for desired messenger RNA (mRNA) but still includes some undesired ribosomal RNA (rRNA). General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995), and in U.S. Pat. No. 7,081,340, issued Jul. 25, 2006, all of which are herein incorporated by reference. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

If necessary, DNA can be removed at various stages of RNA isolation, by DNase or other techniques well known in the art. After analysis of the RNA concentration after purification, RNA repair and/or amplification steps may be performed before subjecting the RNA to further manipulation or analysis. For example, a nucleic acid sample may be a sample in which the mRNA has been amplified by, for example, in vitro transcription. Exemplary methods for RNA amplification are disclosed in U.S. Pat. No. 7,081,340, issued Jul. 25, 2006; U.S. Pub. No. 2005/0196782, published Sep. 8, 2005; and U.S. Pub. No. 2009/0042192, published Feb. 12, 2009, all of which are hereby incorporated by reference. Other methods for RNA amplification known in the art may also be used.

Furthermore, in an embodiment of the invention, the nucleic acid sample is obtained from cells, tissues, organs, or lysates, fractionations, or portions thereof, from any human or non-human animal, and may be fresh, fixed, or frozen. In a particular embodiment, the nucleic acid sample is obtained from a biopsy sample from a human and may be derived from a fine needle, core, or any other types of biopsy. In yet another particular embodiment, the nucleic acid sample is obtained from a fixed paraffin-embedded tissue (FPET) sample from a human.

As used herein, the term "DNA probe" refers to a single-stranded DNA oligonucleotide having a sequence partly or completely complementary to a "target RNA" and specifically hybridizes to the RNA. As used herein, "target RNA" refers to an undesired RNA that is the target for depletion from the nucleic acid sample. The target RNA may be any RNA, including, but not limited to, rRNA, tRNA, and mRNA. DNA probes may be produced by techniques known in the art such as chemical synthesis and by in vitro or in vivo expression from recombinant nucleic acid molecules. The DNA probes may also be produced by amplification of the target RNA, including, but not limited to, RT-PCR, asymmetric PCR, and rolling circle amplification. In an embodiment of the invention, DNA probes are 10 to 100 nucleotides in length. In another embodiment, the DNA probes are 14 to 85 nucleotides in length. In yet another embodiment, the DNA probes are 50 to 80 nucleotides in length. In a further embodiment of the invention, the DNA probes are 60 to 80 nucleotides in length. In yet a further embodiment, a single DNA probe spans the entire length of the target RNA. DNA probes may or may not have regions that are not complementary to a target RNA, so long as such sequences do not substantially affect specific hybridization to the RNA. In another embodiment of the invention, the DNA probe may be complementary to all or part of a target RNA sequence and therefore, there may be more than one DNA probe that specifically hybridizes to the RNA. For example, there may be at least 1, 2, 3, 4, 5, 6, 7, 8, 9, or 10 DNA probes that specifically hybridize to an RNA. In a particular embodiment, at least one DNA probe specifically hybridizes to substantially the entire full length sequence of the target RNA. As used herein, "substantially the entire full length sequence" refers to less than 100% but at least 80%, 81%, 82%, 83%, 84%, 85%, 86%, 87%, 88%, 89%, 90%, 91%, 92%, 93%, 94%, 95%, 96%, 97%, 98%, or 99%, or any range therein, of the full length sequence. In an embodiment of the invention, a multiplicity of DNA probes specifically binds to substantially the entire full length sequence of the target RNA. In yet another embodiment, a multiplicity of DNA probes specifically binds to the entire full length sequence of the target RNA. The DNA probes may be complementary to sequences that overlap one another, or may be complementary to non-overlapping sequences.

As used herein, "specifically hybridizes" refers to a state where a specific DNA probe is able to hybridize with a target RNA, for example, rRNA, over other nucleic acids present in a nucleic acid sample. The DNA probe is first denatured into single-stranded DNA by methods known in the art, for example, by heating or under alkaline conditions, and then hybridized to the target RNA by methods also known in the art, for example, by cooling the heated DNA in the presence of the target RNA. The condition under which a DNA probe specifically hybridizes with an RNA are well known to those of ordinary skill in the art and it will be appreciated that these conditions may vary depending upon factors including the GC content and length of the probe, the hybridization temperature, the composition of the hybridization reagent or solution, and the degree of hybridization specificity sought.

In an embodiment of the invention, the DNA probe is specifically hybridized at a temperature range of between 22° C. and 100° C. In another embodiment of the invention, the DNA probe is specifically hybridized at a temperature range of between 50° C. and 98° C. In yet another embodiment, the DNA probe is specifically hybridized at about 95° C. The hybridization temperature may also be ramped down to stabilize the hybridization. For example, the hybridization temperature may be ramped down at a rate of 0.1° C./sec to 22° C. after hybridization at 95° C.

As used herein, the term "complementary" refers to a nucleic acid comprising a sequence of consecutive nucleobases capable of hybridizing to another nucleic acid strand even if less than all the nucleobases do not base pair with a counterpart nucleobase. In certain embodiments, a "complementary" nucleic acid comprises a sequence in which at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, and any range therein, of the nucleobase sequence is capable of base-pairing with another nucleic acid sequence.

In an embodiment of the invention, a DNA probe may be labeled with a reporter group moiety such as a radioisotope, a fluorescent or chemiluminescent moiety, with an enzyme or ligand, which can be used for detection or confirmation that the probe has hybridized to the target sequence.

In embodiments in which the target RNA is rRNA, the rRNA may be eukaryotic rRNA, and may be either cytoplasmic rRNA or mitochondrial rRNA. Cytoplasmic rRNAs include, for example, 28S, 5.8S, 5S and 18S rRNAs. Mitochondrial rRNAs include, for example, 12S and 16S rRNAs. The rRNA may also be prokaryotic rRNA, which includes, for example, 5S, 16S, and 23S rRNA. The sequences for rRNAs are well known to those skilled in the art and can be readily found in sequence databases such as GenBank or may be found in the literature. For example, the sequence for the human 18S rRNA can be found in GenBank as Accession No. M10098 and the human 28S rRNA as Accession No. M11167.

In another embodiment, the target RNA is transfer RNA (tRNA). In yet another embodiment, the target RNA may be a particular mRNA. For example, it may be desirable to remove cellular transcripts that are usually present in abundance. Thus, the target mRNA includes, but is not limited to, ACTB, GAPDH, and TUBB. Other sequences for tRNA and specific mRNA are well known to those skilled in the art and can be readily found in sequence databases such as GenBank or may be found in the literature.

In a particular embodiment of the invention, mRNA is not targeted for depletion and therefore, the DNA probe does not have a poly-T that will hybridize to the poly-A tail of eukaryotic mRNA. In yet another particular embodiment of the invention, the DNA probe targets and specifically hybridizes to human 18S or human 28S rRNA. Examples of the sequences of the DNA probes targeting the full length sequences of human 18S and human 28S rRNA are shown in Table 1.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

TABLE 1

| Sequence Name | Sequence (5'-3') | Length | SEQ ID NO. |
|---|---|---|---|
| T5319/ 18srRNA.R6 | TTAATCATGGCCTCAGTTCCGAAAACCAACAAAATAGAACCGCGGTCCTATTCCATTATTCCTAGCTGCGGTATCCAGGC | 80 | 1 |
| T5320/ 18srRNA.R6 | GCTTTCGCTCTGGTCCGTCTTGCGCCGGTCCAAGAATTTCACCTCTAGCGGCGCAATACGAATGCCCCCGGCCGTCCCTC | 80 | 2 |
| T5321/ 18srRNA.R6 | TGGTCGGAACTACGACGGTATCTGATCGTCTTCGAACCTCCGACTTTCGTTCTTGATTAATGAAAACATTCTTGGCAAAT | 80 | 3 |
| T5322/ 18srRNA.R6 | TCCTCGTTCATGGGGAATAATTGCAATCCCCGATCCCCATCACGAATGGGGTTCAACGGGTTACCCGCGCCTGCCGGCGT | 80 | 4 |
| T5323/ 18srRNA.R6 | ATCGGTAGTAGCGACGGGCGGTGTGTACAAAGGGCAGGGACTTAATCAACGCAAGCTTATGACCCGCACTTACTGGGAAT | 80 | 5 |
| T5324/ 18srRNA.R6 | TTCGACCGTCTTCTCAGCGCTCCGCCAGGCCGTGGGCCGACCCCGGCGGGGCCGATCCGAGGGCCTCACTAAACCATCCA | 80 | 6 |
| T5325/ 18srRNA.R6 | GGGGGCTCGAGGACGGGCCCGGCGCCCCGCAAGCGAGGAGGACGACGGACGG | 56 | 7 |
| T5326/ 18srRNA.R6 | TTTGAGACAAGCATATGCTACTGGCAGGATCAACCAGGTAGGTAGGTAGAGCGCGGCGAGGCCCCGACGCGGCCGGACGG | 80 | 8 |
| T5327/ 18srRNA.R6 | AAGGAACCATAACTGATTTAATGAGCCATTCGCAGTTTCACTGTACCGGCCGTGCGTACTTAGACATGCATGGCTTAATC | 80 | 9 |
| T5328/ 18srRNA.R6 | CGAAGGGGGTCAGCGCCCGTCGGCATGTATTAGCTCTAGAATTACCACAGTTATCCAAGTAGGAGAGGAGCGAGCGACCA | 80 | 10 |
| T5329/ 18srRNA.R6 | CCGCGGCCCGCCCCCCGGCCGGGGCCGGAGAGGGGCTGACCGGGTTGGTTTTGATCTGATAAATGCACGCATCCCCCCCG | 80 | 11 |
| T5330/ 18srRNA.R6 | TAGGGCAGACGTTCGAATGGGTCGTCGCCGCCACGGGGGCGTGCGATCGGCCCGAGGTTATCTAGAGTCACCAAAGCCG | 80 | 12 |
| T5331/ 18srRNA.R6 | CTCCCTCTCCGGAATCGAACCCTGATTCCCCGTCACCCGTGGTCACCATGGTAGGCACGGCGACTACCATCGAAAGTTGA | 80 | 13 |
| T5332/ 18srRNA.R6 | TTCGTCACTACCTCCCCGGGTCGGGAGTGGGTAATTTGCGCGCCTGCTGCCTTCCTTGGATGTGGTAGCCGTTTCTCAGG | 80 | 14 |
| T5333/ 18srRNA.R6 | CTCCAATGGATCCTCGTTAAAGGATTTAAAGTGGACTCATTCCAATTACAGGGCCTCGAAAGAGTCCTGTATTGTTATTT | 80 | 15 |
| T5334/ 18srRNA.R6 | CTACGAGCTTTTTAACTGCAGCAACTTTAATATACGCTATTGGAGCTGGAATTACCGCGGCTGCTGGCACCAGACTTGCC | 80 | 16 |
| T5335/ 18srRNA.R6 | AGGGGGCGCCGAGAGGCAAGGGGCGGGACGGGCGGTGGCTCGCCTCGCGGCGGACCGCCCGCCCGCTCCCAAGATCCAA | 80 | 17 |
| T5336/ 18srRNA.R6 | GGCTCGGGCCTGCTTTGAACACTCTAATTTTTTCAAAGTAAACGCTTCGGGCCCCGCGGGACACTCAGCTAAGAGCATCG | 80 | 18 |
| T5337/ 18srRNA.R6 | ACCCAAAGACTTTGGTTTCCCGGAAGCTGCCCGGCGGGTCATGGGAATAACGCCGCCGCATCGCCGGTCGGCATCGTTTA | 80 | 19 |
| T5338/ 18srRNA.R6 | TAAGCCGCAGGCTCCACTCCTGGTGGTGCCCTTCCGTCAATTCCTTTAAGTTTCAGCTTTGCAACCATACTCCCCCCGGA | 80 | 20 |
| T5339/ 18srRNA.R6 | CACGGAATCGAGAAAGAGCTATCAATCTGTCAATCCTGTCCGTGTCCGGGCCGGGTGAGGTTTCCCGTGTTGAGTCAAAT | 80 | 21 |
| T5340/ 18srRNA.R6 | AGCATGCCAGAGTCTCGTTCGTTATCGGAATTAACCAGACAAATCGCTCCACCAACTAAGAACGGCCATGCACCACCACC | 80 | 22 |
| T5341/ 18srRNA.R6 | TCAATCTCGGGTGGCTGAACGCCACTTGTCCCTCTAAGAAGTTGGGGGACGCCGACCGCTCGGGGTCGCGTAACTAGTT | 80 | 23 |

TABLE 1-continued

| Sequence Name | Sequence (5'-3') | Length | SEQ ID NO. |
|---|---|---|---|
| T5342/18srRNA.R6 | AGGGTAGGCACACGCTGAGCCAGTCAGTGTAGCGCGCGTGCAGCCCCGGACATCTAAGGGCATCACAGACCTGTTATTGC | 80 | 24 |
| T5343/18srRNA.R6 | TAATGATCCTTCCGCAGGTTCACCTACGGAAACCTTGTTACGACTTTTACTTCCTCTAGATAGTCAAG | 68 | 25 |
| T5344/28srRNA.R3 | GGAATCCTGGTTAGTTTCTTTTCCTCCGCTGACTAATATGCTTAAATTCAGCGGGTCGCCACGTCTGATCTGAGGTCGCG | 80 | 26 |
| T5345/28srRNA.R3 | TTCCGTACGCCACATGTCCCGCGCCCCGCGGGGCGGGGATTCGGCGCTGGGCTCTTCCCTGTTCACTCGCCGTTACTGAG | 80 | 27 |
| T5346/28srRNA.R3 | TACCGGCCTCACACCGTCCACGGGCTGGGCCTCGATCAGAAGGACTTGGGCCCCCACGAGCGGCGCCGGGGAGCGGGTC | 80 | 28 |
| T5347/28srRNA.R3 | TTAGATGGAGTTTACCACCCGCTTTGGGCTGCATTCCCAAGCAACCCGACTCCGGGAAGACCCGGGCGCGCGCCGGCCGC | 80 | 29 |
| T5348/28srRNA.R3 | CTTGAACTCTCTCTTCAAAGTTCTTTTCAACTTTCCCTTACGGTACTTGTTGACTATCGGTCTCGTGCCGGTATTTAGCC | 80 | 30 |
| T5349/28srRNA.R3 | GCCGGACCCGCCGCCGGGTTGAATCCTCCGGGCGGACTGCGCGGACCCCACCCGTTTACCTCTTAACGGTTTCACGCCCT | 80 | 31 |
| T5350/28srRNA.R3 | GGGGCGGCGGGGGAAGGGAGGGCGGGTGGAGGGGTCGGAGGAACGGGGGGCGGGAAAGATCCGCCGGGCCGCCGACACG | 80 | 32 |
| T5351/28srRNA.R3 | TCCCCCGCCGACCCCACCCCCGGCCCCGCCCGCCCACCCCCGCACCCGCCGGAGCCCGCCCCCTCCGGGGAGGAGGAGGA | 80 | 33 |
| T5352/28srRNA.R3 | TCCCAGCCGTCCCGGAGCCGGTCGCGGCGCACCGCCTGGAAATGCGCCCGGCGGCGGCCGGTCGCCGGTCCGGGGACGG | 80 | 34 |
| T5353/28srRNA.R3 | GGGGCCGGGGGGCGGAGACGGGGGAGGAGGAGGACGGACGGACGGACGGGGCCCCCCGAGCCACCTTCCCCGCCGGGCCT | 80 | 35 |
| T5354/28srRNA.R3 | CGGTCCCGCCGCCCCGCCGCCGCCGCCACCGCCGCCGCCGCCGCCGCCCCGACCCGCGCGCCCTCCCGAGGGAGGACGC | 80 | 36 |
| T5355/28srRNA.R3 | CGGCGACGGGTCTCGCTCCCTCGGCCCCGGGATTCGGCGAGTGCTGCTGCCGGGGGGGCTGTAACACTCGGGGGGGTTT | 80 | 37 |
| T5356/28srRNA.R3 | AGGAGACGCCGGCGCCGCGCCGGGGGAGACCCCCCTCGCGGGGATTCCCGCGGGGTGGGCGCCGGGAGGGGGAGAGCG | 80 | 38 |
| T5357/28srRNA.R3 | CCCGTCGCCGGGGCGGGGCGCGGGGAGGAGGGGTGGGAGAGCGGTCGCGCCGTGGGAGGGGTGGCCCGGCCCCCCCACG | 80 | 39 |
| T5358/28srRNA.R3 | CCCCGGGCCCGACGGCGCGACCCGCCCGGGGCGCACTGGGACAGTCCGCCCCGCCCCCGACCCGCGCGCGGCACCCCC | 80 | 40 |
| T5359/28srRNA.R3 | CCGACGTCGCCGCCGACCCCGTGCGCTCGCTCCGCCGTCCCCCTCTTCGGGGACGCGCGCGTGGCCCCGAGAGAACCTC | 80 | 41 |
| T5360/28srRNA.R3 | CGGCGGCTTTCGTGCGAGCCCCCGACTCGCGCACGTGTTAGACTCCTTGGTCCGTGTTTCAAGACGGGTCGGGTGGGTAG | 80 | 42 |
| T5361/28srRNA.R3 | GGTGCCCCTCGGCGGACTGGAGAGGCCTCGGGATCCCACCTCGGCCGGCGAGCGCGCCGGCCTTCACCTTCATTGCGCCA | 80 | 43 |
| T5362/28srRNA.R3 | GGCATAGTTCACCATCTTTCGGGTCCTAACACGTGCGCTCGTGCTCCACCTCCCCGGCGCGGCGGGCGAGACGGGCCGGT | 80 | 44 |
| T5363/28srRNA.R3 | TACCCAGGTCGGACGACCGATTTGCACGTCAGGACCGCTACGGACCTCCACCAGAGTTTCCTCTGGCTTCGCCCTGCCCA | 80 | 45 |
| T5364/28srRNA.R3 | TCTGCGAGAGCGCCAGCTATCCTGAGGGAAACTTCGGAGGGAACCAGCTACTAGATGGTTCGATTAGTCTTTCGCCCCTA | 80 | 46 |
| T5365/28srRNA.R3 | ATAGGTTGAGATCGTTTCGGCCCCAAGACCTCTAATCATTCGCTTTACCGGATAAAACTGCGTGGCGGGGTGCGTCGGG | 80 | 47 |
| T5366/28srRNA.R3 | AAAGTGGCCCACTAGGCACTCGCATTCCACCCCGGCTCCACGCCAGCGAGCCGGGCTTCTTACCCATTTAAAGTTTGAGA | 80 | 48 |

TABLE 1-continued

| Sequence Name | Sequence (5'-3') | Length | SEQ ID NO. |
|---|---|---|---|
| T5367/28srRNA.R3 | TTCTGGGGTCTGATGAGCGTCGGCATCGGGCGCCTTAACCCGGCGTTCGGTTCATCCCGCAGCGCCAGTTCTGCTTACCA | 80 | 49 |
| T5368/28srRNA.R3 | GCAGGTGAGTTGTTACACACTCCTTAGCGGATTCCGACTTCCATGGCCACCGTCCTGCTGTCTATATCAACCAACACCTT | 80 | 50 |
| T5369/28srRNA.R3 | CGTCCACTCTCGACTGCCGGCGACGGCCGGGTATGGGCCCGACGCTCCAGCGCCATCCATTTTCAGGGCTAGTTGATTCG | 80 | 51 |
| T5370/28srRNA.R3 | CCCACACCCCCGCCGCCGCCGCCGCCGCCCTCCGACGCACACCACACGCGCGCGCCGCCGCCGCCCCCGCCGCTCC | 80 | 52 |
| T5371/28srRNA.R3 | TCCGCGGGGCTCCGGGGGCGGGGAGCGGGGCGTGGGCGGGAGGAGGGAGGAGGCGTGGGGGGGGGCGGGGAAGGAC | 80 | 53 |
| T5372/28srRNA.R3 | CCTGCGGCGGCCTCCACCCGGGCCCGCGCCCTAGGCTTCAAGGCTCACCGCAGCGGCCCTCCTACTCGTCGCGGCGTAGC | 80 | 54 |
| T5373/28srRNA.R3 | TGCTGTTCACATGGAACCCTTCTCCACTTCGGCCTTCAAAGTTCTCGTTTGAATATTTGCTACTACCACCAAGATCTGCA | 80 | 55 |
| T5374/28srRNA.R3 | CCGAGGGCAACGGAGGCCATCGCCCGTCCCTTCGGAACGGCGCTCGCCCATCTCTCAGGACCGACTGACCCATGTTCAAC | 80 | 56 |
| T5375/28srRNA.R3 | GTTACCGCACTGGACGCCTCGCGGCGCCCATCTCCGCCACTCCGGATTCGGGGATCTGAACCCGACTCCCTTTCGATCGG | 80 | 57 |
| T5376/28srRNA.R3 | CCATTCCAGGGCGCCCTGCCCTTCACAAAGAAAAGAGAACTCTCCCCGGGGCTCCCGCCGGCTTCTCCGGGATCGGTCGC | 80 | 58 |
| T5377/28srRNA.R3 | TCAAGGGCCAGCGAGAGCTCACCGGACGCCGCCGGAACCGCGACGCTTTCCAAGGCACGGGCCCCTCTCTCGGGGCGAAC | 80 | 59 |
| T5378/28srRNA.R3 | CCAGAGGCTGTTCACCTTGGAGACCTGCTGCGGATATGGGTACGGCCCGGCGCGAGATTTACACCCTCTCCCCCGGATTT | 80 | 60 |
| T5379/28srRNA.R3 | CCCAGCCCTTAGAGCCAATCCTTATCCCGAAGTTACGGATCCGGCTTGCCGACTTCCCTTACCTACATTGTTCCAACATG | 80 | 61 |
| T5380/28srRNA.R3 | TGCCCCGGGCGTGGGGGGGCGCGCGCCTCGTCCAGCCGCGGCGCGCGCCCAGCCCCGCTTCGCGCCCCAGCCCGACCGA | 80 | 62 |
| T5381/28srRNA.R3 | AGAGAGAGAGAGAGGGCGCGGGGTGGGGAGGGAGCGAGCGGCGCGCGCGGGTGGGGCGGGGAGGGCCGCGAGGGGGG | 80 | 63 |
| T5382/28srRNA.R3 | CCTGCCGCCCCGACCCTTCTCCCCCCGCCGCGCCCCACGCGCGCTCCCCGGGGAGGGGGAGGACGGGGAGCGGGGG | 80 | 64 |
| T5383/28srRNA.R3 | GCCGCCGGCCCCCCGGGTCCCCGGGGCCCCCCTCGCGGGGACCTGCCCCCGCCGGCCGCCCCGGCGGCCGCCGCGCGGCC | 80 | 65 |
| T5384/28srRNA.R3 | CTCCCCGGGGGCGGCCGCGACGCCCGCCGCAGCTGGGCGATCCACGGGAAGGGCCCGGCTCGCGTCCAGAGTCCGCGCC | 80 | 66 |
| T5385/28srRNA.R3 | CGACCGCTCCCGCCCCCAGCGGACGCGCGCGCGACCGAGACGTGGGGTGGGGGTGGGGGCGCGCCGCGCCGCCGCCGGG | 80 | 67 |
| T5386/28srRNA.R3 | GAACGGGGGCGGACGGGGCCGGGGGGTAGGGCGGGGGACGAACCGCCCCGCCCCGCCGCCCGCCGACCGCCGCCGCC | 80 | 68 |
| T5387/28srRNA.R3 | GGCGGACCCGGCGGGGGGACCGGCCCGCGGCCCCTCCGCCGCCTGCCGCCGCCGCCGCGCGCCGAGGAGGAGGGGG | 80 | 69 |
| T5388/28srRNA.R3 | ATTCCCCTGGTCCGCACCAGTTCTAAGTCGGCTGCTAGGCGCCGGCCGAGGCGAGGCGCGCGCGGAACCGCGGCCCCGGG | 80 | 70 |
| T5389/28srRNA.R3 | TCAGAGCACTGGGCAGAAATCACATCGCGTCAACACCCGCCGCGGGCCTTCGCGATGCTTTGTTTTAATTAAACAGTCGG | 80 | 71 |
| T5390/28srRNA.R3 | GAGGCATTTGGCTACCTTAAGAGAGTCATAGTTACTCCCGCCGTTTACCCGCGCTTCATTGAATTTCTTCACTTTGACAT | 80 | 72 |
| T5391/28srRNA.R3 | TGGCTGTGGTTTCGCTGGATAGTAGGTAGGGACAGTGGGAATCTCGTTCATCCATTCATGCGCGTCACTAATTAGATGAC | 80 | 73 |

TABLE 1-continued

| Sequence Name | Sequence (5'-3') | Length | SEQ ID NO. |
|---|---|---|---|
| T5392/ 28srRNA.R3 | CATGTCTCTTCACCGTGCCAGACTAGAGTCAAGCTCAACAGGGTCTTCTTTCCCCGCTGATTCCGCCAAGCCCGTTCCCT | 80 | 74 |
| T5393/ 28srRNA.R3 | CAGGGCCGCGGACCCCGCCCCGGGCCCCTCGCGGGGACACCGGGGGGGCGCCGGGGGCCTCCCACTTATTCTACACCTCT | 80 | 75 |
| T5394/ 28srRNA.R3 | AGAGCCCCTCGGGCTCGCCCCCCCGCCTCACCGGGTCAGTGAAAAAACGATCAGAGTAGTGGTATTTCACCGGCGGCCCG | 80 | 76 |
| T5395/ 28srRNA.R3 | CGCCCCAGTCAAACTCCCCACCTGGCACTGTCCCCGGAGCGGGTCGCGCCCGGCCGGGCGGGCGCTTGGCGCCAGAAGCG | 80 | 77 |
| T5396/ 28srRNA.R3 | TTGCCCTTCTGCTCCACGGGAGGTTTCTGTCCTCCCTGAGCTCGCCTTAGGACACCTGCGTTACCGTTTGACAGGTGTAC | 80 | 78 |
| T5397/ 28srRNA.R3 | AAACCCAAAAGGTCAGAAGGATCGTGAGGCCCCGCTTTCACGGTCTGTATTCGTACTGAAAATCAAGATCAAGCGAGCTT | 80 | 79 |
| T5398/ 28srRNA.R3 | CAAAAAGCGACGTCGCTATGAACGCTTGGCCGCCACAAGCCAGTTATCCCTGTGGTAACTTTTCTGACACCTCCTGCTTA | 80 | 80 |
| T5399/ 28srRNA.R3 | CGTTCCCTATTAGTGGGTGAACAATCCAACGCTTGGCGAATTCTGCTTCACAATGATAGGAAGAGCCGACATCGAAGGAT | 80 | 81 |
| T5400/ 28srRNA.R3 | CTGAGCAGGATTACCATGGCAACAACACATCATCAGTAGGGTAAAACTAACCTGTCTCACGACGGTCTAAACCCAGCTCA | 80 | 82 |
| T5401/ 28srRNA.R3 | CCCACAGATGGTAGCTTCGCCCCATTGGCTCCTCAGCCAAGCACATACACCAAATGTCTGAACCTGCGGTTCCTCTCGTA | 80 | 83 |
| T5402/ 28srRNA.R3 | CCGAGGCCAACCGAGGCTCCGCGGCGCTGCCGTATCGTTCGCCTGGGCGGGATTCTGACTTAGAGGCGTTCAGTCATAAT | 80 | 84 |
| T5403/ 28srRNA.R3 | GCGGGGCACGCGCCCTCCCGCGGCGGGGCGCGTGGAGGGGGGGCGGCCCGCCGGCGGGGACAGGCGGGGGACCGGCTAT | 80 | 85 |
| T5404/ 28srRNA.R3 | AGGGGGCGGCCGCCTTTCCGGCCGCGCCCCGTTTCCCAGGACGAAGGGCACTCCGCACCGGACCCCGGTCCCGGCGCGCG | 80 | 86 |
| T5405/ 28srRNA.R3 | CGAAACCCCGACCCAGAAGCAGGTCGTCTACGAATGGTTTAGCGCCAGGTTCCCCACGAACGTGCGGTGCGTGACGGGCG | 80 | 87 |
| T5406/ 28srRNA.R3 | GACAAACCCTTGTGTCGAGGGCTGACTTTCAATAGATCGCAGCGAGGGAGCTGCTCTGCTACGTA | 65 | 88 |

FIG. 1 illustrates an embodiment of the invention. A nucleic acid sample is contacted with at least one DNA probe complementary to a target RNA. Upon hybridization, the DNA probe forms a complex with the target RNA and forms a DNA-RNA hybrid. In one embodiment, the DNA probe specifically hybridizes with an rRNA and forms a DNA-rRNA hybrid. In another embodiment, the DNA probe specifically hybridizes with a tRNA and forms a DNA-tRNA hybrid. In yet another embodiment, the DNA specifically hybridizes with an mRNA and forms a DNA-mRNA hybrid.

The DNA-RNA hybrid is then depleted from the nucleic acid sample. For example, in some embodiments, a ribonuclease (RNAse) that specifically targets DNA-RNA hybrids is used to deplete the DNA-RNA hybrid. In a specific embodiment of the invention, RNAse H is used to specifically hydrolyze the RNA in the DNA-RNA hybrid so that the RNA becomes degraded. The remaining DNA is then available to hybridize with another RNA target sequence. In an embodiment of the invention, the RNAse H is a thermostable RNAse H. RNAse H may be obtained commercially, including, for example, Hybridase™ (EPICENTRE Biotechnologies, Madison, Wis.).

In an embodiment of the invention, the RNAse H is allowed to degrade the DNA-RNA hybrid at a temperature range of between 32° C. and 70° C. In another embodiment, the RNAse H is allowed to degrade the DNA-RNA hybrid at a temperature range of between 37° C. and 60° C. In yet another embodiment, RNAse H is allowed to degrade the DNA-RNA hybrid at a temperature of about 37° C.

The DNA probe hybridization step and the RNA degradation step with RNAse H may be repeated.

If desired, the DNA may also be removed by addition of an enzyme that specifically targets and digests DNA. In an embodiment of the invention, a DNAse is used. In a specific embodiment of the invention, the DNAse is DNAse I. DNAses may be obtained commercially.

Upon depletion of the undesired nucleic acid, the sample will contain an enriched population of the desired nucleic acid. In an embodiment of the invention, the undesired nucleic acid comprises less than 20%, 19%, 18%, 17%, 16% 15%, 14%, 13%, 12%, 11% 10%, 9%, 8%, 7%, 6%, 5%, 4%, 3%, 2%, or 1%, or any range therein, of the total nucleic acid in the sample after depletion of the undesired nucleic acid. Thus, the enriched population of the desired nucleic acid may comprise at least 99%, 98%, 97%, 96%, 95%, 94%, 93%, 92%, 91%, 90%, 89%, 88%, 87%, 86%, 85%, 84%, 83%, 82%, 81%, or 80%, or any range therein, of the total nucleic acid in the sample. For example, in a particular embodiment, the undesired nucleic acid is rRNA and comprises less than 10% of all RNA present in the sample. In another particular embodiment, the undesired nucleic acid is tRNA. In yet another particular embodiment, the undesired nucleic acid is mRNA.

Once the desired nucleic acid has been enriched, it may be further purified using methods known in the art, including, for example, commercially available purification kits such as the RNEasy MinElute column (QIAGEN, Valencia, Ca.) or the MasterPure complete DNA/RNA purification kit (Epicentre Technologies, WI).

In an embodiment of the invention, the enriched population of nucleic acids may be amplified by methods known in the art. Exemplary methods for DNA amplification include ligase chain reaction, strand displacement, and polymerase chain reaction (PCR), including quantitative PCR. Exemplary methods for RNA amplification include in vitro transcription, including those described in U.S. Pat. No. 7,081,340, issued Jul. 25, 2006; U.S. Pub. No. 2005/0196782, published Sep. 8, 2005; and U.S. Pub. No. 2009/0042192, published Feb. 12, 2009, all of which are hereby incorporated by reference.

In a further embodiment of the invention, the enriched population can be used to prepare cDNA according to methods known to those of ordinary skilled in the art. The cDNA may be used for subsequent manipulation and/or analysis, including, but not limited to, amplification, library preparation, sequencing, and gene expression analysis. Prior to further analysis or manipulation, the cDNA may optionally be purified by methods known in the art, including commercially available purification kits, such as the PCR MinElute column (QIAGEN, Valencia, Ca.).

The conversion of mRNA to cDNA typically involves the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using gene specific primers, random hexamers, or oligo-dT primers, depending on the circumstances and the goal of expression profiling. The primers may additionally contain an adaptor sequence that allows the detection or identification of the synthesized cDNA or its amplification product. Use of adaptor sequences in primers is well-known in the art. Extracted RNA can be reverse-transcribed using commercially available kits, such as the GeneAmp RNA PCR kit (Perkin Elmer, CA, USA), following the manufacturer's instructions. The derived cDNA can then be used as a template in a subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Th polymerase to hydrolyze a hybridization probe bound to its target amplicon, but any enzyme with equivalent 5' nuclease activity can be used. Two oligonucleotide primers are used to generate an amplicon typical of a PCR reaction. Again, the primers may additionally contain an adaptor sequence that allows the detection of the amplified product. A third oligonucleotide, or probe, may also be used to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In an embodiment of the invention, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A variation of the RT-PCR technique is the real-time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Heid et al., *Genome Research* 6:986-994 (1996).

Microarray techniques may also be used for gene expression analysis. In this method, polynucleotide sequences of interest (such as cDNAs and oligonucleotides) are plated, or arrayed, on a microchip substrate. In a specific embodiment of the microarray technique, PCR amplified cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology.

The development of microarray methods for large-scale analysis of gene expression makes it possible to search systematically for molecular markers of cancer classification and outcome prediction in a variety of tumor types. A potential benefit of RNA-depleted samples includes the application of microarray analysis to FPET samples, which have previously proven difficult. Thus, the method of the invention can be performed on a variety of nucleic acid samples including those obtained from for example, cells, tissues, organs, or lysates, fractionations, or portions thereof. In a particular embodiment, the nucleic acid sample is obtained from a fixed paraffin-embedded tissue (FPET) sample. The FPET sample may be obtained from a tumor. In an embodiment of the invention, the tumor is a cancer. In another embodiment, the cancer is selected from breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

Despite the availability of commercial products, and the extensive knowledge available concerning the isolation of RNA from tissues, isolation of nucleic acid from FPET samples and its use are not without difficulty. mRNA is often difficult to extract and maintain in its native state. Consequently, mRNA recovered from various biological sources, particularly from archived, fixed paraffin-embedded tissue (FPET), is often fragmented and/or degraded. RNA degradation progresses with archive storage time and results in RNA having an average size of about 100 bases after 17 years of storage. By comparison, intact mRNA has an average size of about 1800-2000 bases.

Typically, extraction of mRNA is followed by conversion to cDNA using the primer dependent enzyme reverse transcriptase (RT). Universal conversion of intact mRNA to cDNA is performed by oligo dT priming of the mRNA in the presence of RT. Priming with oligo dT is made possible by the presence of a poly A tract at the 3' end of mRNA. However, it has been found that FPET mRNA is inefficiently converted to cDNA by oligo dT priming and may be due to the fact that the majority of the degraded mRNAs does not contain a polyA tail. Nevertheless, it has been shown that the degraded RNA can still be efficiently profiled for gene expression using gene-specific primers (GSP). This indicates that most regions of the expressed genes are present in the randomly fragmented RNA in proportions expected for the intact mRNA. This suggests that it should be possible to perform effective universal gene expression profiling on fragmented, e.g. FPET mRNA extracts.

To this end, it has been attempted to globally reverse transcribe FPET RNA by first polyadenylating the RNA and then performing oligo dT primed RT. Polyadenylation of FPET RNA prior to oligo dT priming increased the conversion of the RNA to cDNA by about 2-4-fold. This result has been interpreted to suggest that polyadenylation may be a useful method to prepare fragmented RNA, e.g. FPET RNA, for global reverse transcription and subsequent gene expression profiling. However, polyadenlyation can also prime other RNA, such as rRNA. Moreover, the signal amplification was still only a small fraction of that obtained by priming with gene specific primers (GSP).

Thus, in an embodiment of the invention, the method of the invention is useful for depleting undesired sequences from an FPET sample that contains a mixture of sequences, thereby enriching for a population of interest. The method comprises contacting a nucleic acid sample obtained from an FPET sample with at least one DNA probe complementary to an RNA. The DNA probe specifically hybridizes to the target RNA and forms a DNA-RNA hybrid. The sample is then contacted with an RNase H, and the RNase H degrades the RNA in the DNA-RNA hybrid. In one embodiment, the DNA probe specifically hybridizes with an rRNA and forms a DNA-rRNA hybrid. In another embodiment, the DNA probe specifically hybridizes with a tRNA and forms a DNA-tRNA hybrid. In yet another embodiment, the DNA probe specifically hybridizes with an mRNA and forms a DNA-mRNA hybrid. In a specific embodiment, the DNA probe(s) specifically hybridizes with substantially the entire full length sequence of the target RNA or to the entire full length sequence of the target RNA. Optionally, the sample may be contacted with a DNase after RNA depletion to degrade the DNA probe.

The present invention also provides compositions and kits for depleting RNA from a nucleic acid sample. As an example of a composition of the invention, the composition comprises DNA probes complementary to a target RNA. In an embodiment of the invention, the composition comprises DNA probes that specifically hybridize to substantially the entire full length sequence or to the entire full length sequence of a target RNA. In a specific embodiment, the composition comprises DNA probes of SEQ ID NOs: 1-25. In another embodiment, the composition comprises DNA probes of SEQ ID NOs: 26-88. In yet another embodiment, the composition comprises DNA probes of SEQ ID NOs: 1-88.

Any of the compositions of the invention may be comprised in a kit. For example, a composition comprising the DNA probes of SEQ ID NOs: 1-88 may be comprised in a kit. The kit will thus comprise, in a suitable container, the DNA probes of the invention. The kit may also include one or more buffers, such as a hybridization buffer, components for amplifying RNA, such as primers, as well as components for preparing a cDNA library. The kit may further include instructions for using the kit components.

The present invention is illustrated by the following Examples, which are not intended to be limiting in any way.

Example 1

Figure 2:
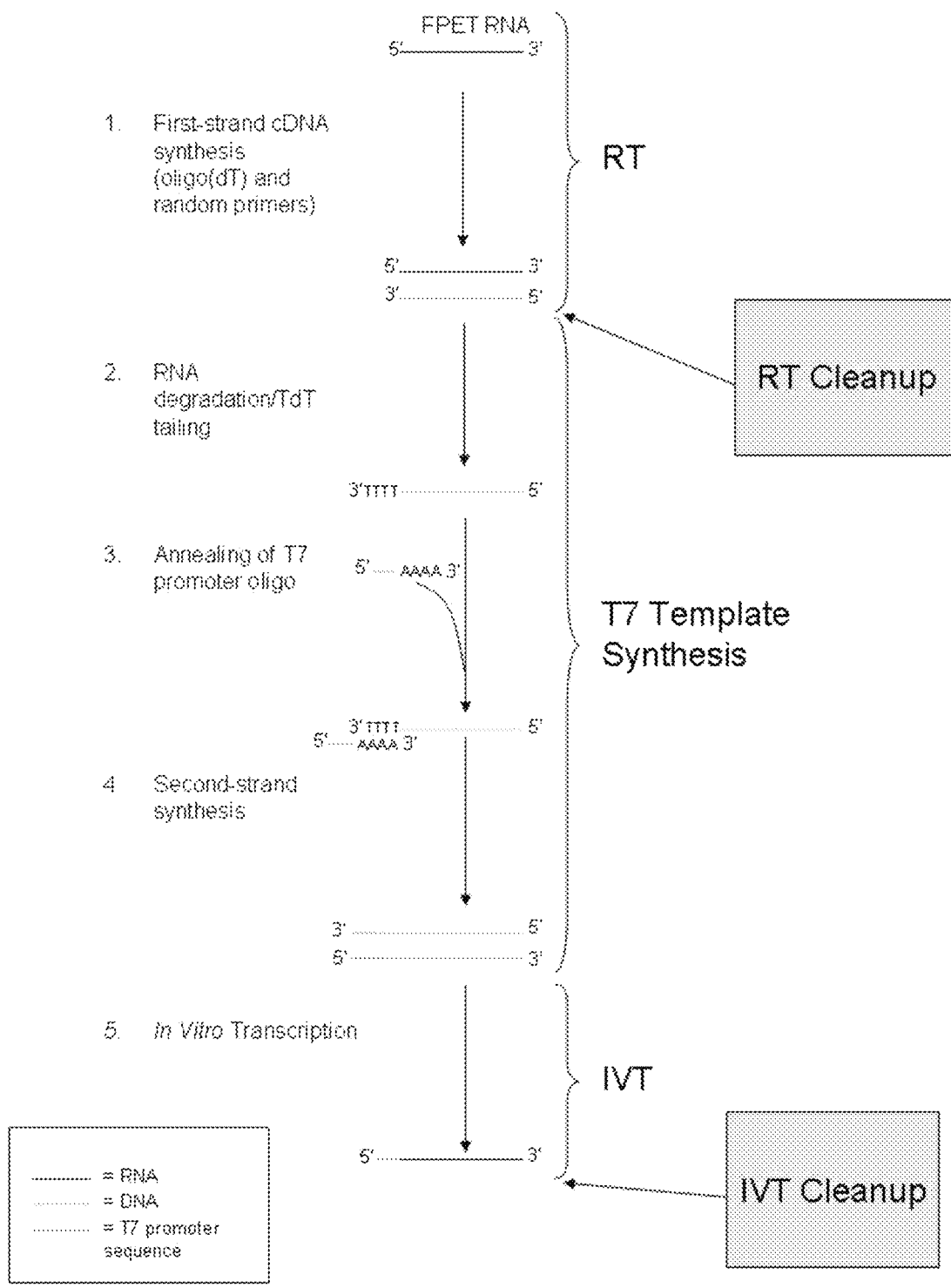
FIG. 2 is a schematic illustration of a method for amplifying RNA.

Depletion of 18s and 28s rRNA from Amplified RNA Obtained from Fixed Paraffin-Embedded Tissue (FPET) Samples of Colon Cancer Patients Samples A single, commercially available FPET block from a colon cancer patient (ProteoGenex, Culver City, Calif.) was used as the source of RNA for all samples in this Example. Total RNA was extracted from the tissue block using the MasterPure™ Kit (Epicentre Biotechnologies, Madison, Wis.). The total RNA was amplified as outlined in FIG. 2 and described in U.S. Pub. No. 2005/0196782, published Sep. 8, 2005, and U.S. Pub. No. 2009/0042192, published Feb. 12, 2009. Briefly, either 25 ng or 50 ng of an RNA sample was converted to cDNA via reverse transcription using oligo dT and random nonamers. The RNA was then degraded by incubation with RNase H and the cDNA was poly-dT tailed through the action of a terminal deoxynucleotidyl transferase (TdT) enzyme. A T7 RNA polymerase promoter sequence was then hybridized to the tailed cDNA, and made double-stranded through the activity of DNA polymerase. This double-stranded cDNA was then used as a template for in vitro transcription. The process generally yields as much as 100 µg of amplified RNA per sample. This amplified RNA maintains a high degree of similarity with the original source material RNA, but contains a T7 RNA polymerase promoter sequence appended at the end of each strand. Thus, the amplified RNA can be used as a surrogate for the source material.

Depletion of 18S and 28S rRNA from the Amplified RNA Sample

The amplified RNA was depleted of 18S and 28S rRNA, with or without further DNAse I treatment. Four different samples were generated and are described in Table 2:

TABLE 2

| # | Sample Name | Description |
|---|---|---|
| 1 | Not Depleted | Amplified RNA, not depleted |
| 2 | Depleted Method1 | Amplified RNA, depleted, no DNAse I |
| 3 | Depleted Method2 | Amplified RNA, depleted, DNAse I-treated |
| 4 | Depleted Method2 rep | Replicate of #3 |

One microgram of the amplified RNA obtained was mixed with an equimolar mixture of the eighty-eight synthetic DNA probes shown in Table 1. Taken together, the 88 DNA probes represent the entire full length complementary sequence of human 18s rRNA (GenBank accession M10098) and human 28s rRNA (GenBank accession M11167). The mixture was heated and then cooled in a manner that produces double-stranded DNA-RNA hybrids. The mixture was then incubated with RNAse H under appropriate buffer components at a defined temperature for a defined period of time. The mixture was then incubated with DNAse I under appropriate buffer components at a defined temperature for a defined period of time. The mixture was then purified to remove protein from the RNA preparations. The procedure is outlined as follows:

1. Denature and slow-cool RNA/probe mix
   a. In one 200 uL PCR tube, the following were added:
      1 microgram total RNA from FPET
      937 nanograms rRNA antisense DNA probe pool
      1 µL 5× Hybridization Buffer (500 mM Trizma-HCl; 1M NaCl)
   The mixture was brought to a final volume of 5 µL with nuclease-free water.
   b. The mixture was incubated as follows using a thermocycler with a heated lid:
      95° C. for 2 minutes
      Ramp to 22° C. at 0.1° C./second
      Place on ice
2. RNAse H Digestion
   a. The following were added to the RNA/probe mix from step 1.b above:
      10 units Hybridase™ (Epicentre, Madison, Wis.) RNAse H
      1 µL 10× Hybidase Buffer 2 (500 mM Trizma-HCl; 1M NaCl; 200 mM MgCl$_2$)

The mixture was brought to a final volume of 10 µL with nuclease-free water.
   b. The mixture was incubated as follows using a thermocycler with a heated lid:
      37° C. for 30 minutes
      Place on ice
   c. The sample was purified using an RNEasy MinElute column (QIAGEN, Valencia, Calif.) according to manufacturer's instructions. The purified sample had a final volume of approximately 12 µL.
3. DNAseI Treatment
   a. The following were added to the purified RNA in step 2.c:
      4 units DNAseI (NEB, Ipswich, Mass.)
      2 uL 10×NEB Buffer
   Nuclease-free water was added to bring the volume to 20 µL
   b. The mixture was incubated as follows using a thermocycler with a heated lid:
      37° C. for 30 minutes
      Place on ice
   c. The sample was purified using an RNEasy MinElute column (QIAGEN, Valencia, Calif.) according to manufacturer's instructions. The purified sample had a final volume of approximately 12 µL.

Figure 3:
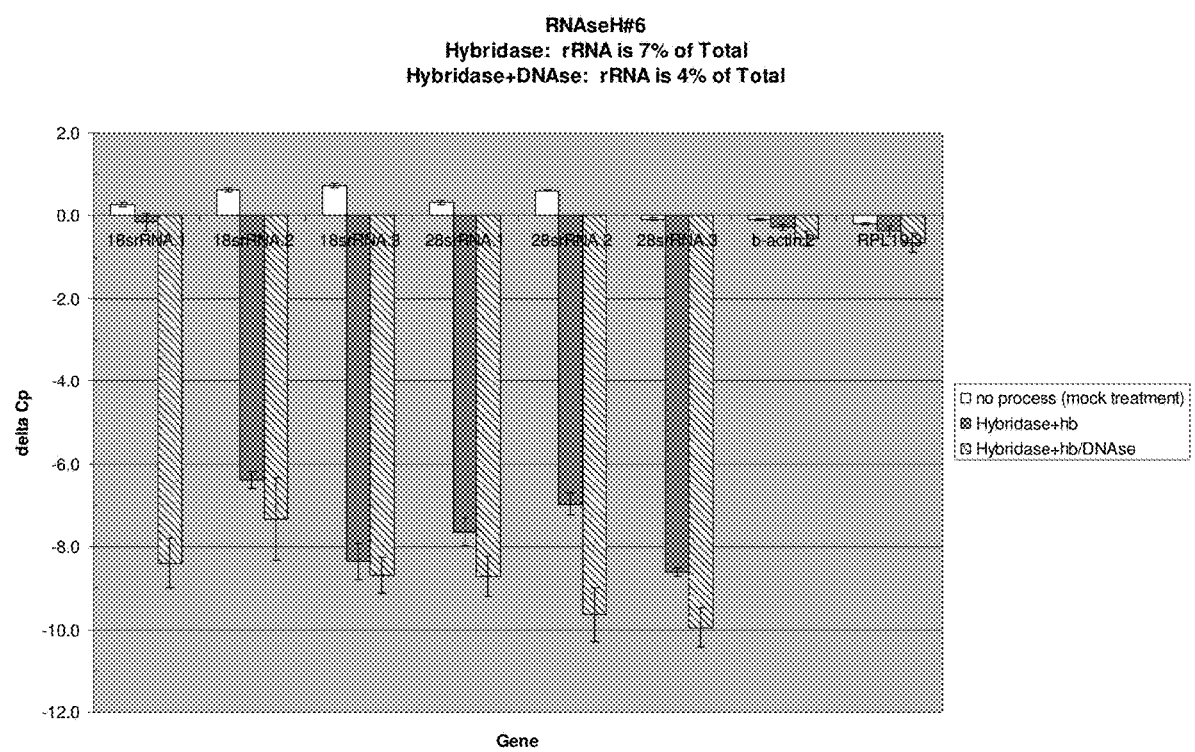
FIG. 3 is a graph showing the relative abundance of 18S and 28S rRNA in mock treated (blank boxes), RNase H-treated (filled boxes), and RNase H and DNase I-treated (hatched boxes) samples. RT-PCR was performed on each sample in triplicate for three different regions of 18S and 28S rRNAs. β-actin and RPL were used as controls.

RT-PCR was performed on the samples to determine relative abundance of the 18S and 28S rRNA. FIG. 3 shows the relative rRNA depletion in samples that were mock treated (Sample #1; blank boxes); treated with RNAse H (Sample #2; filled boxes); or treated with RNAse H followed by DNAse I treatment (Sample #3; hatched boxes). RT-PCR of three different regions of 18S and 28S was performed in triplicate on each sample. β-actin and RPL were used as controls. RNAse H treatment, with or without subsequent DNAse I treatment, reduced the abundance of 18S and 28S rRNA from the samples, while the mock-treated sample showed little or no reduction in the rRNAs. After RNAse H treatment, the 18S and 28S comprised an average of 7% of total RNA in the sample. After RNAse H and DNAse I treatment, the 18S and 28S comprised an average of 4% of total RNA in the sample. RNAse H and DNAse I treatments had little effect on the control genes.

Figure 4:
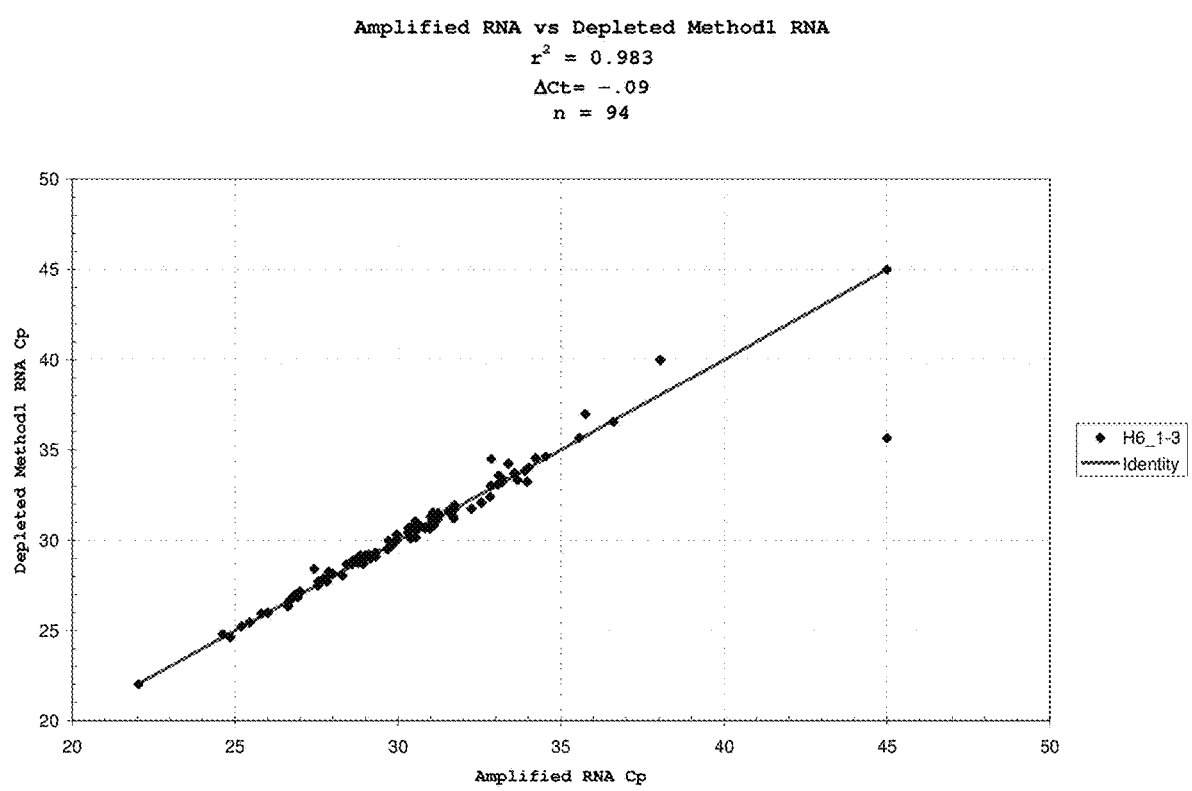
FIG. 4 shows the average difference correlation between amplified RNA before rRNA-depletion ("amplified RNA") and after rRNA-depletion ("depleted method1 RNA").

To demonstrate that rRNA depletion does not alter the gene expression profiles, correlation graphs were prepared using average difference values for 93 or 94 genes in amplified RNA and rRNA-depleted amplified RNA. A perfect correlation between different samples would be indicated by an $r^2$ value of 1. FIG. 4 shows the average difference correlation comparing the results of amplified RNA without rRNA depletion (Sample #1; "Amplified RNA" in the x-axis) and rRNA-depleted amplified RNA without DNAse I treatment (Sample #2; "Depleted Method1 RNA" in the y-axis) over 96 genes. Genes that did not meet the detection threshold were excluded. The $r^2$ value in this case was 0.983 over 94 genes, indicating a good correlation between the two samples.

Figure 5:
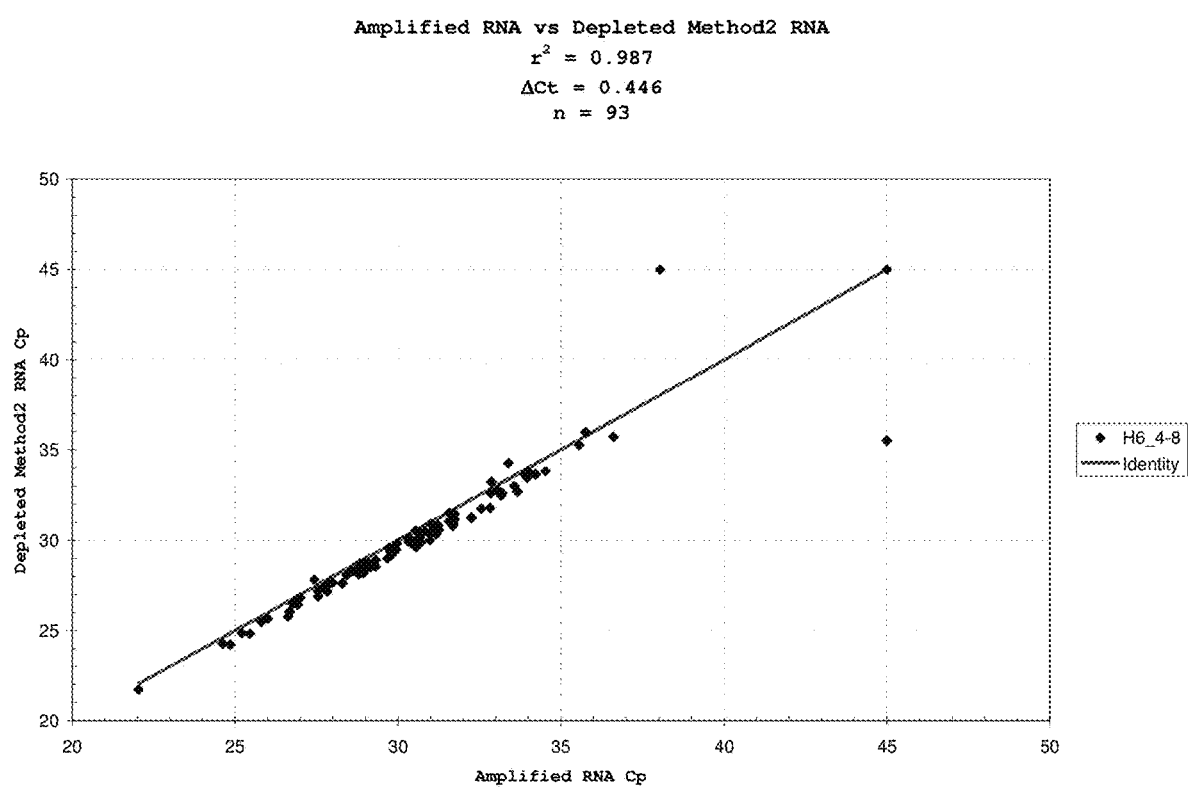
FIG. 5 shows the average difference correlation between amplified RNA before rRNA-depletion ("amplified RNA") and after rRNA-depletion and DNase I treatment ("depleted method2 RNA").

FIG. 5 shows the average difference correlation comparing the results of amplified RNA without rRNA depletion (Sample #1; "Amplified RNA" in the x-axis) and rRNA-depleted amplified RNA with DNAse I treatment (Sample #3; "Depleted Method2 RNA" in the y-axis) over 93 detectable genes. Again, the $r^2$ value in this case was 0.987, indicating a good correlation between the two samples.

Example 2

Figure 6:
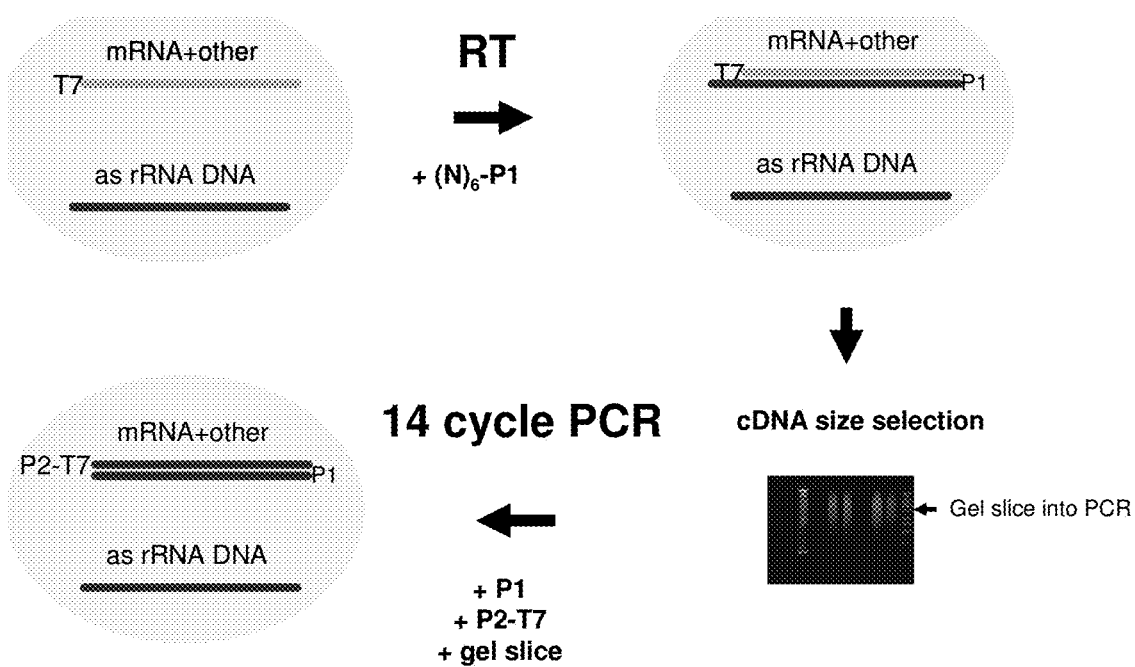
FIG. 6 is a schematic illustration of a method for preparing a cDNA library from amplified RNA.

Preparation of cDNA Libraries from rRNA-Depleted Amplified RNA Obtained from FPET As illustrated in FIG. 6, the amplified RNA from Example 1 was reverse-transcribed with adaptor (P1)-modified random hexamers (P1-N6 primer) (P1: 5'-AGATCG-GAAGAGCGTCGTGTAGGGAAAGAGTGTA-GATCTCGGTGGTCGCC GTATCATT-3') (SEQ ID NO: 89) to produce cDNA. The cDNA was resolved on a 6% TBE-Urea gel and the region from 116-200 bp was excised and cut into four equal slices. PCR was performed on one slice using the P1 primer and an adaptor (P2)-modified T7 primer (P2-T7 primer) containing an intervening nucleotide "barcode" between the P2 and T7 sequences that serves to identify each sample (P2: 5'-CAAGCAGAAGACGGCA TACGAGAT-3') (SEQ ID NO: 90); (T7: 5'-GGGA-GACGCGTGTAAA-3') (SEQ ID NO: 91). The PCR reaction was then purified. The procedure is outlined below.

1. First-strand cDNA synthesis
   a. Primer hybridization. The following were mixed:
      500 ng amplified, rRNA-depleted RNA
      2 µL of a 2 uM solution of P1-N6 primer
      Brought to 5 µL with nuclease-free water.
   b. The mixture was incubated as follows using a thermocycler with a heated lid:
      37° C. for 10 minutes
      Place on ice
   c. Reverse Transcription. The following were mixed:
      2 µL 5× RT Buffer (Invitrogen, Carlsbad, Calif.)
      1 µL DTT (20 mM)
      1 µL dNTP mix (10 mM each)
      1 µL SuperScript II™ (Invitrogen, Carlsbad, Calif.)
      5 µL RNA/primer mix from step 1.b
   d. The mixture was incubated as follows using a thermocycler with a heated lid:
      20° C. for 10 minutes
      37° C. for 10 minutes
      42° C. for 45 minutes
      96° C. for 5 minutes
      Place on ice
2. cDNA Purification/Size Selection
   a. The cDNA reaction from step 1.d was purified using a PCR MinElute column (QIAGEN, Valencia, Calif.) according to manufacturer's instructions. The final eluate volume was 10 µL.
   b. 5 µL of the sample from step 2.a was mixed with 5 µL 2× gel loading buffer. The mixture was incubated as follows using a thermocycler with a heated lid:
      95° C. for 3 minutes
      Place on ice
   c. The reaction from step 2.b was loaded onto one lane of a 1 mm thick 6% TBE-Urea gel and run for 17 minutes at 180 Volts or until the leading dye front reached the middle of the gel. Molecular weight ladders were also run in adjacent lanes. The gel was stained in 1:10,000 SYBR-Gold for 10 minutes.
   d. Using a razor blade, the portion of the lane containing the sample that corresponded to a molecular weight of from 116-200 nt was excised and further vertically subdivided into four approximately equal slices.
3. PCR Amplification
   a. Each slice was mixed with the following:
      2 µL dNTP mix (10 mM ea.)
      10 µL 10×PCR Advantage™ (Clontech, Mountain View, Calif.) Buffer
      3 µL of an 8 uM solution of P1-N6 PCR primer
      3 µL of an 8 uM solution of P2-T7 PCR primer
      2 µL Advantage™ (Clontech, Mountain View, Calif.) DNA polymerase
      80 µL nuclease-free water
   b. The mixture was incubated as follows using a thermocycler with a heated lid:
      1 cycle
         94° C. for 1 minute
      2 cycles
         94° C. for 15 seconds
         55° C. for 30 seconds
         72° C. for 30 seconds
      12 cycles
         94° C. for 15 seconds
         62° C. for 30 seconds
         72° C. for 30 seconds
      1 cycle
         72° C. for 7 minutes
   c. cDNA was purified using a PureLink™ PCR Micro Purification Kit (Invitrogen, Carlsbad, Calif.) according to manufacturer's instructions.

Table 3 shows the yield of the cDNA libraries prepared from each amplified RNA sample of Table 2.

TABLE 3

| Yield (ng)* | | | |
|---|---|---|---|
| Not Depleted | Depleted Method1 | Depleted Method2 | Depleted Method2 rep |
| 732 | 308 | 848 | 877 |

*Based on using half the size-selected RT rxn. Potential yield is twice what is shown.

Table 4 shows the insert lengths of a number of clones analyzed (n) from the cDNA libraries prepared from each amplified RNA sample of Table 2.

TABLE 4

| | Insert length** | | | |
|---|---|---|---|---|
| | Not Depleted | Depleted Method1 | Depleted Method2 | Depleted Method2 rep |
| Avg | 82.9 | 77.8 | 74.2 | 60.2 |
| Median | 81 | 90 | 79 | 73 |
| Max | 122 | 139 | 109 | 116 |
| Min | 35 | 6 | 19 | 5 |
| n | 13 | 20 | 18 | 25 |
| # <50 bp | 1 | 4 | 3 | 9 |

**Excludes the TdT tail, present at the 5'-end of all amplified RNA transcripts. Inserts of 50-134 bp were targeted.

As shown in FIGS. 4 and 5, the average difference correlation between amplified RNA without rRNA-depletion (Sample #1) and amplified RNA with rRNA-depletion (Sample #2) or rRNA-depleted amplified RNA with DNAse I treatment (Sample #3) exhibited good correlation ($r^2$=0.983 and 0.987, respectively). The correlation between the rRNA-undepleted and -depleted samples indicates that the gene expression profiles were not altered by the rRNA depletion step. Average difference correlations were also determined in the cDNA libraries prepared from the samples shown in Table 2. Results are shown in Table 5.

TABLE 5

| Library Correlations | | | | |
|---|---|---|---|---|
| | Amplified RNA | | Undepleted Library | |
| | $r^2$* | n | $r^2$** | n |
| Undepleted Library | 0.480 | 84 | 1 | 96 |
| Depleted Method 1 Library | 0.569 | 88 | 0.908 | 82 |
| Depleted Method 2 Library | 0.579 | 88 | 0.928 | 84 |
| Depleted Method 2 Library rep | 0.623 | 92 | 0.933 | 84 |

*Library preparation alters profile
**Alterations are consistent and reproducible library preps As shown in Table 5, the average difference correlations between amplified RNA before cDNA library preparation and amplified RNA after library preparation exhibited low correlation, indicating that the gene expression profile is different in the cDNA library preparation compared to the starting material. Without being bound to theory, this may be due to the possibility that the cDNA insert size in the library is smaller than the region that some of the PCR primers are able to bind. However, the alterations were consistent and reproducible across the library preparations.

Clones from each cDNA library were also sequenced. The results are shown in Table 6. In the cDNA library prepared from rRNA-undepleted RNA (Sample #1), 13 clones were sequenced, of which seven mapped to the 18S/28S rRNA, and six mapped to mitochondrial genes. Thus, 54% of the clones sequenced from the rRNA-undepleted library constituted 18S/28S rRNA. In contrast, approximately 4% or less of the clones sequenced from the rRNA-depleted libraries mapped to 18S/28S rRNAs. Moreover, there was an increase in the percentage of clones that mapped to known genes ("refseq": 30-56%).

TABLE 6

| | Not Depleted | | Depleted Method1 | | Depleted Method2 | | Depleted Method2 Replicate | |
|---|---|---|---|---|---|---|---|---|
| Sequencing Summary | # Clones | % | # Clones | % | # Clones | % | # Clones | % |
| mapped to refseq | 0 | 0% | 6 | 30% | 10 | 56% | 8 | 32% |
| mapped to genome | 0 | 0% | 0 | 0% | 1 | 6% | 0 | 0% |
| 18s/28s rRNA | 7 | 54% | 0 | 0% | 0 | 0% | 1 | 4% |
| 5s rRNA | 0 | 0% | 1 | 5% | 1 | 6% | 0 | 0% |
| Mitochondrial | 6 | 46% | 9 | 45% | 6 | 33% | 10 | 40% |
| not mapped/too short | 0 | 0% | 1 | 5% | 0 | 0% | 4 | 16% |
| poor sequence quality | 0 | 0% | 3 | 15% | 0 | 0% | 2 | 8% |
| Total | 13 | 100% | 20 | 100% | 18 | 1 | 25 | 100% |

Method 1: Hybridase ™
Method 2: Hybridase ™ + DNAse
Targeted for depletion: 18s/28s rRNA Example 3

Depletion of 18s and 28s rRNA from Amplified RNA Obtained from Fixed Paraffin-Embedded Tissue (FPET) Samples of Breast Cancer Patients Samples Two breast cancer FPET blocks were obtained from Providence-St. Joseph Medical Center, Burbank Calif., and were used as the source of RNA for all samples in this Example. Total RNA was extracted from the tissue block using the MasterPure™ Kit (Epicentre Biotechnologies, Madison, Wis.) and the total RNA was amplified as described in Example 1. The RNAs were classified as "Lo ER" (exhibiting low EstR1 gene expression) or "Hi ER" (exhibiting high EstR1 gene expression).

Figure 7:
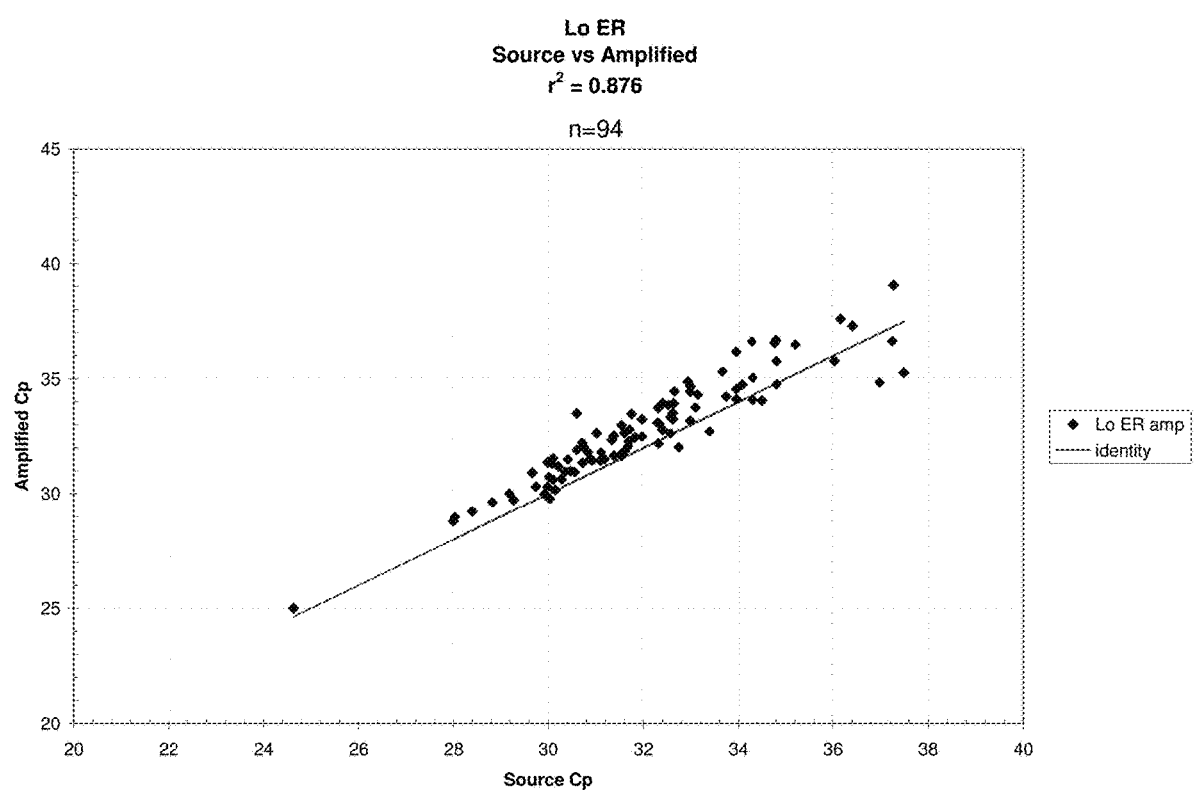
FIG. 7 shows the average difference correlation of total unamplified RNA ("source") versus amplified Lo ER RNA ("amplified").
Figure 8:
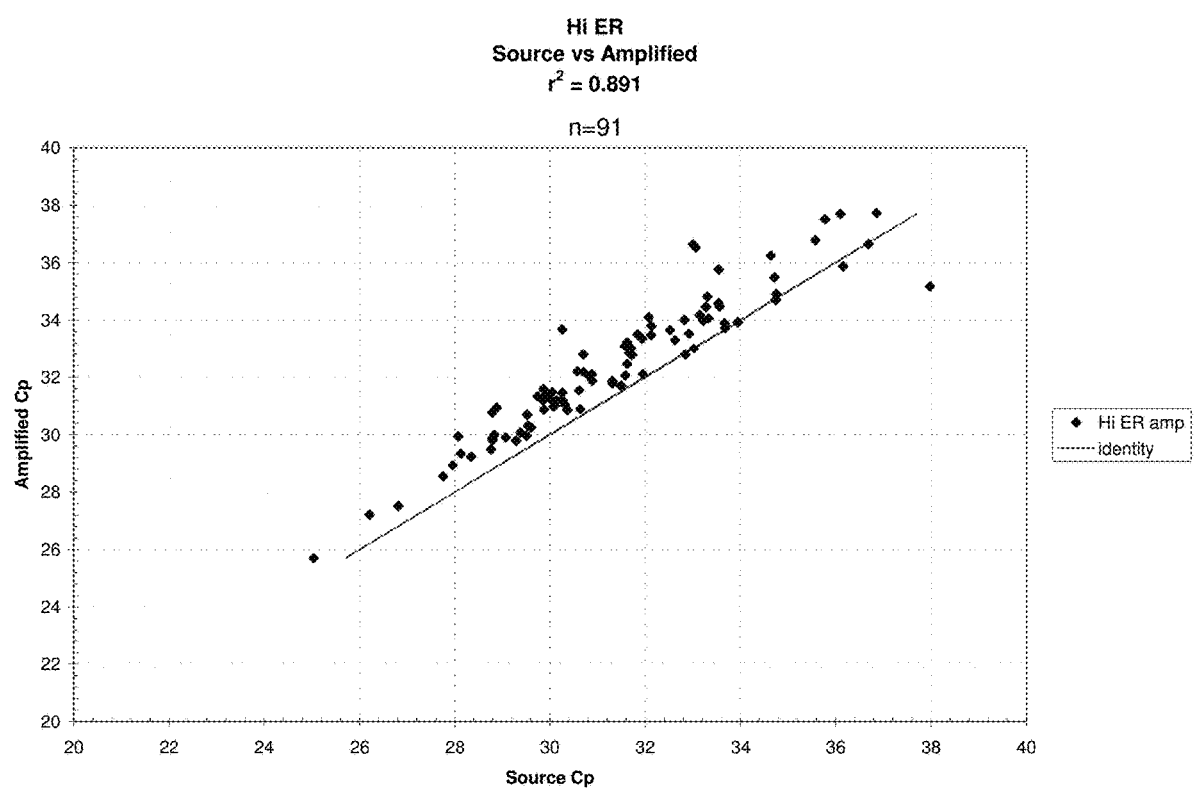
FIG. 8 shows the average difference correlation of total unamplified RNA ("source") versus amplified Hi ER RNA ("amplified").

FIGS. 7 and 8 show the average difference correlation of total unamplified RNA vs amplified Lo ER RNA or amplified Hi ER RNA, respectively, over 96 genes. Genes that did not meet the detection threshold were excluded. The $r^2$ values were 0.876 and 0.891, respectively.

Depletion of 18S and 28S rRNA from the Amplified RNA Sample

The "Lo ER" and "Hi ER" amplified RNA were mixed in different ratios to create additional samples for library preparation. The amplified RNAs were depleted of 18S and 28S rRNA and all samples were treated with DNAse I. The following eight amplified RNA samples were generated:

TABLE 7

| # | Sample Name | Description |
|---|---|---|
| 1 | Lo ER n = 1 | Lo ER amplified RNA, DNAse I treated |
| 2 | Lo ER n = 2 | Replicate of #1 |
| 3 | Hi ER n = 1 | Hi ER amplified RNA, DNAse I treated |
| 4 | Hi ER n = 2 | Replicate of #3 |
| 5 | Lo/Hi 50/50 n = 1 | Mixed amplified RNA, DNAse I treated |
| 6 | Lo/Hi 50/50 n = 2 | Replicate of #5 |
| 7 | Lo/Hi 75/25 n = 1 | Mixed amplified RNA, DNAse I treated |
| 8 | Lo/Hi 75/25 n = 2 | Replicate of #7 |

The amplified RNAs were depleted for 18S and 28S according to Example 1. All of the amplified RNAs were also treated with DNAse I using the RNAse-free DNAse Set (Qiagen, Valencia, Calif.). After step 2b in Example 1, 10 µl of each amplified RNA was mixed with 77.5 µl of $H_2O$, 10 µl Buffer RDD, and 2.5 µl of the DNAse I stock and incubated for 10 minutes at room temperature. The samples were then purified using an RNEasy MinElute column (QIAGEN, Valencia, Calif.) according to manufacturer's instructions. The purified sample had a final volume of approximately 12 µL.

Figure 9:
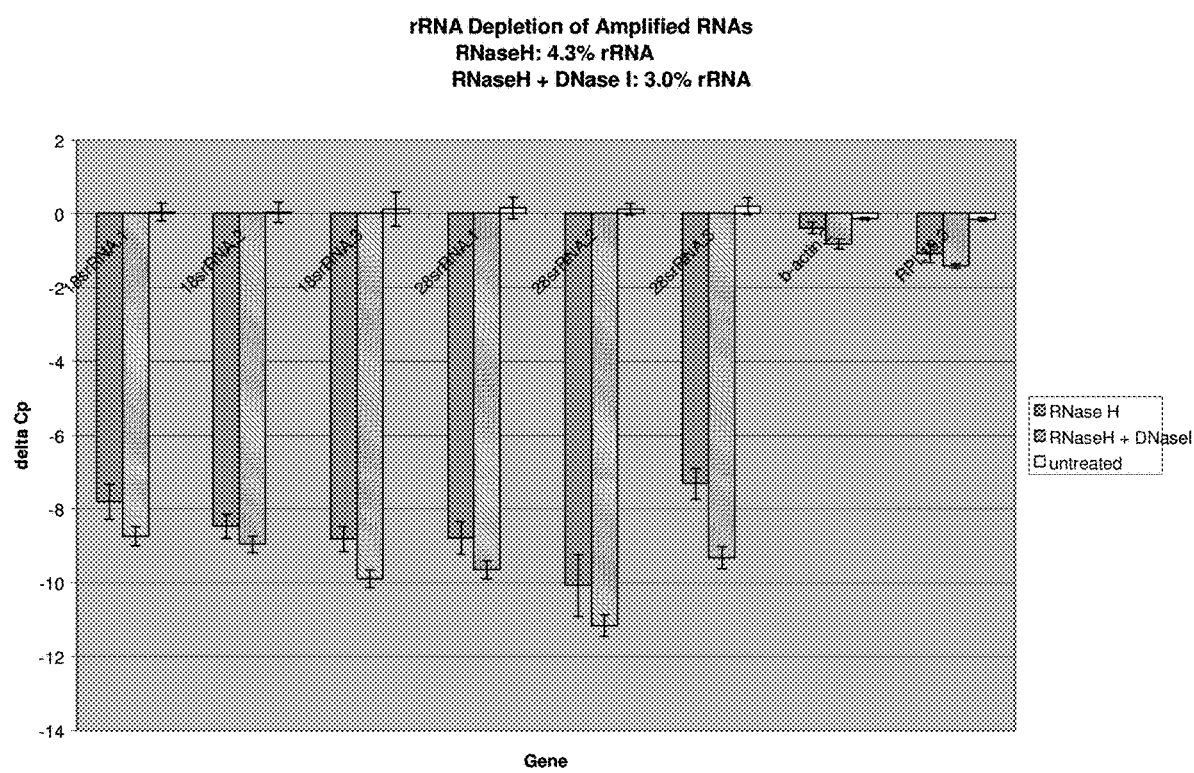
FIG. 9 is a graph showing the relative abundance of 18S and 28S rRNA in untreated (blank boxes), RNase H-treated (filled boxes), and RNase H and DNase I-treated (hatched boxes) samples. RT-PCR was performed on each sample in triplicate for three different regions of 18S and 28S rRNAs. β-actin and RPL were used as controls.

RT-PCR was performed for three different regions of 18S and 28S in triplicate on each type of sample (Lo ER, Hi ER, Lo/Hi 50/50, and Lo/Hi 75/25) to determine relative abundance of the 18S and 28S rRNA before and after DNAse I treatment. Relative rRNA depletion of the 4 samples was averaged. FIG. 9 shows the relative rRNA depletion in untreated samples (blank boxes); treated with RNAse H (filled boxes); or treated with RNAse H followed by DNAse I treatment (hatched boxes). β-actin and RPL were used as controls. RNAse H treatment, with or without subsequent DNAse I treatment, reduced the abundance of 18S and 28S rRNA from the samples, while the untreated sample showed little or no reduction in the rRNAs. After RNAse H treatment, the 18S and 28S comprised an average of 4.3% of total RNA in the sample. After RNAse H and DNAse I treatment, the 18S and 28S comprised an average of 3.0% of total RNA in the sample. RNAse H and DNAse I treatments had little effect on the control genes.

Figure 10:
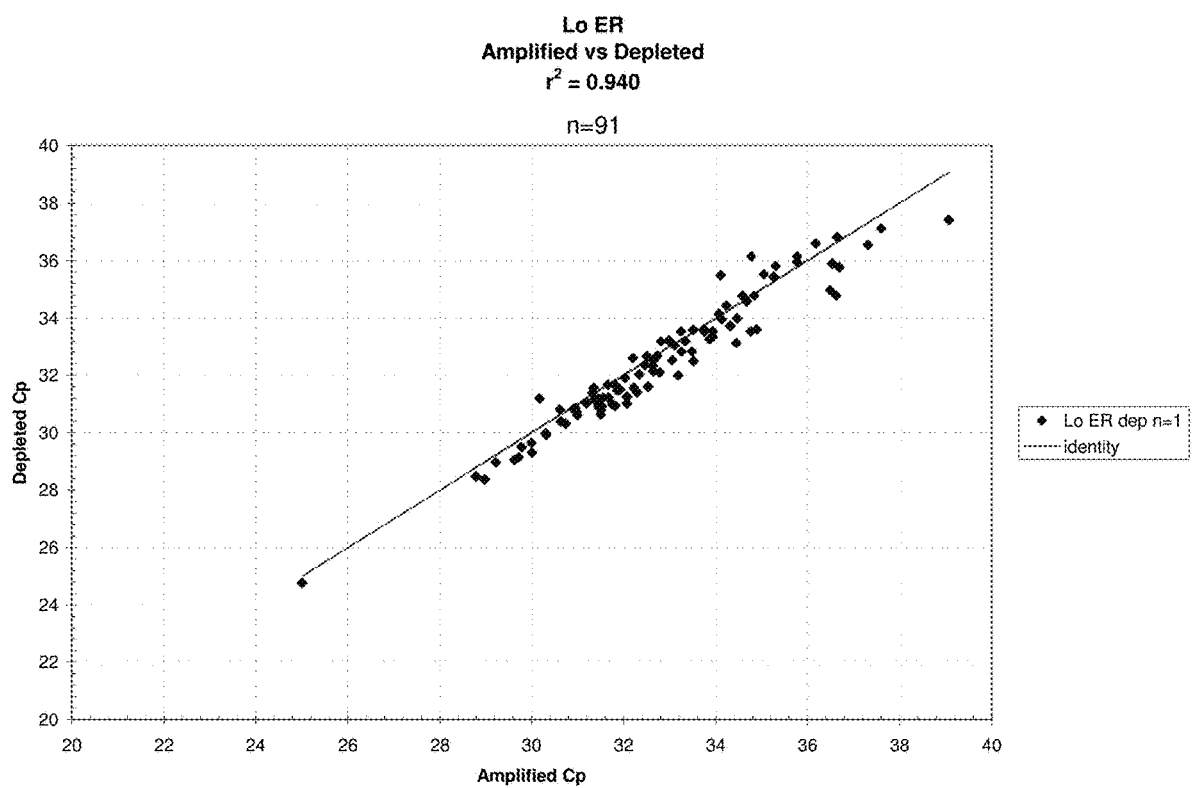
FIG. 10 shows the average difference correlation of rRNA-undepleted Lo ER amplified RNA and rRNA-depleted Lo ER amplified RNA treated with DNase I.

To demonstrate that rRNA depletion does not alter the gene expression profiles, correlation graphs were prepared using average difference values for 96 genes in amplified RNA and rRNA-depleted amplified RNA. A perfect correlation between different samples would be indicated by an $r^2$ value of 1. FIG. 10 shows the average difference correlation comparing the results of rRNA-undepleted Lo ER amplified RNA ("Amplified" in the x-axis) and rRNA-depleted Lo ER amplified RNA with DNAse I treatment (Sample #1; "Depleted" in the y-axis) over 96 genes. Genes that did not meet the detection threshold were excluded. The $r^2$ value in this case was 0.940, indicating a good correlation between the two samples.

Figure 11:
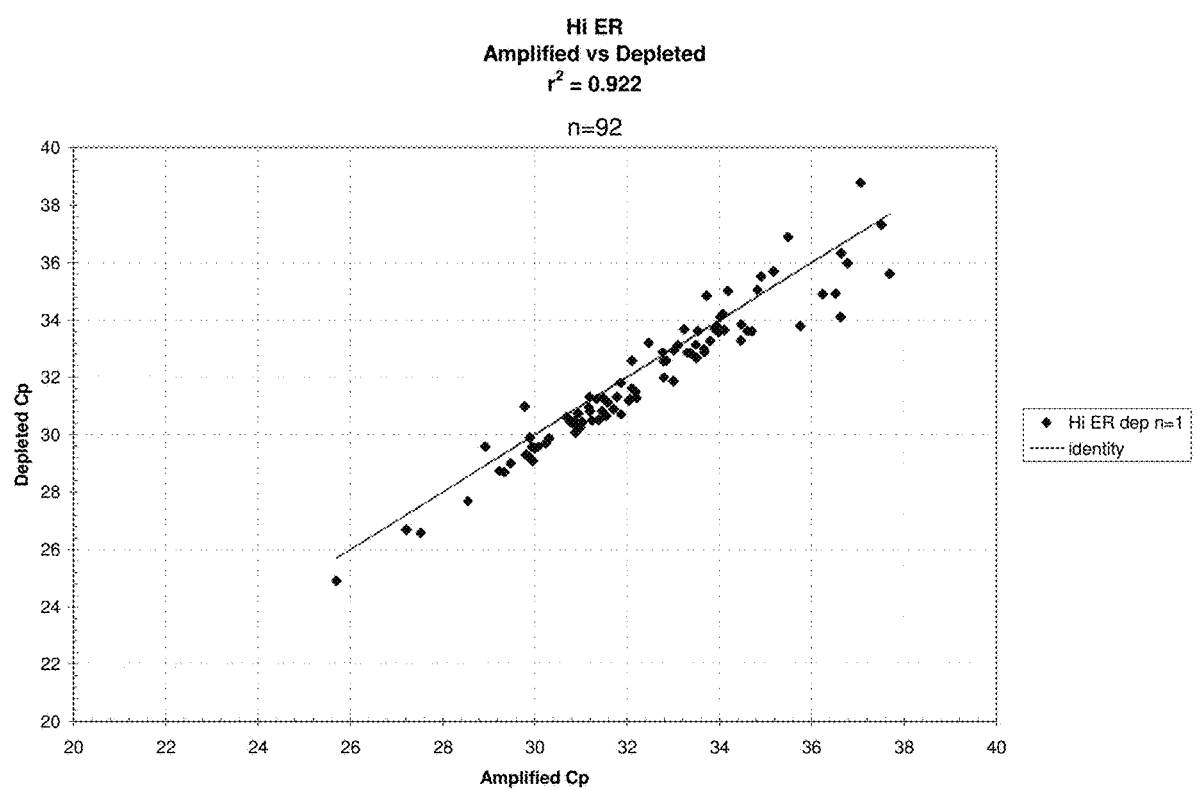
FIG. 11 shows the average difference correlation of rRNA-undepleted Hi ER amplified RNA and rRNA-depleted Hi ER amplified RNA treated with DNase I.

FIG. 11 shows the average difference correlation comparing the results of rRNA-undepleted Hi ER amplified RNA ("Amplified" in the x-axis) and rRNA-depleted Hi ER amplified RNA with DNAse I treatment (Sample #3; "Depleted" in the y-axis) over 96 genes. Genes that did not meet the detection threshold were excluded. The $r^2$ value in this case was 0.922, indicating a good correlation between the two samples.

Figure 12:
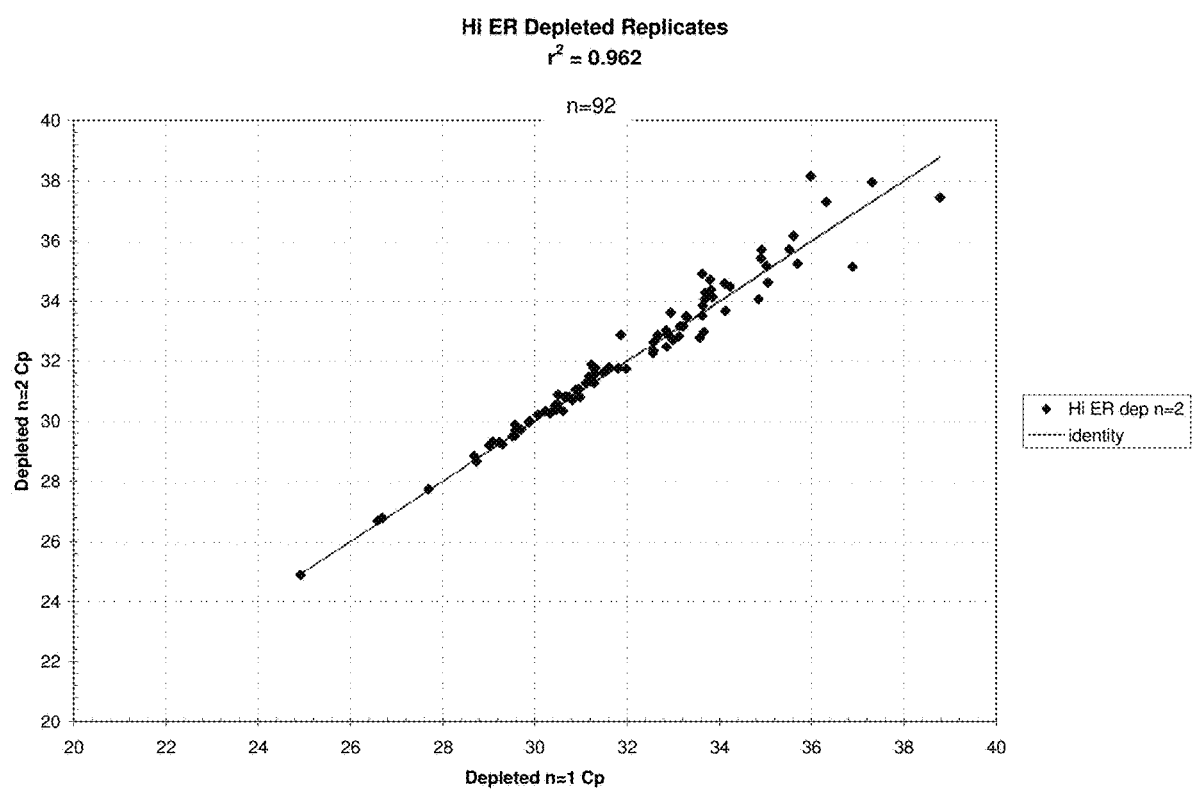
FIG. 12 shows the average difference correlation of duplicates of rRNA-depleted Hi ER amplified RNA.

FIG. 12 shows the average difference correlation comparing the results of duplicates of rRNA-depleted Hi ER amplified RNA (Sample #3 and #4; "Depleted n=1" in the x-axis and "Depleted n=2" in the y-axis, respectively) over 96 genes. Genes that did not meet the detection threshold were excluded. The $r^2$ value in this case was 0.962, indicating a good correlation between the duplicate samples.

Example 4

Figure 13:
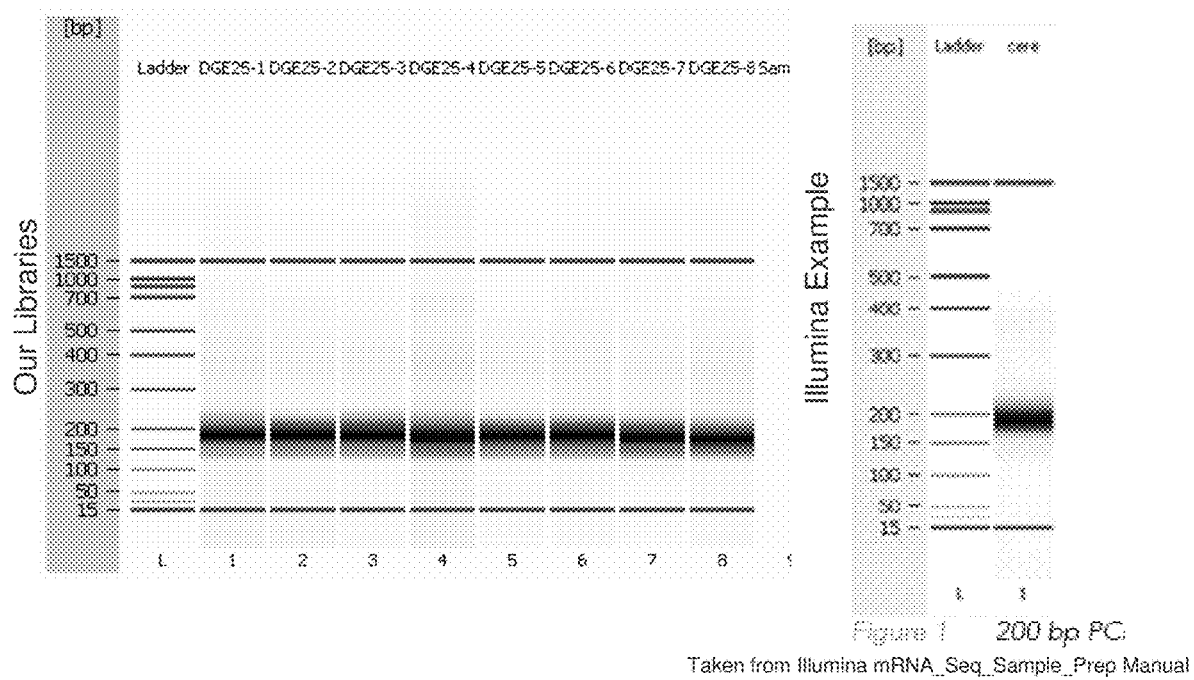
FIG. 13 shows a comparison of the size distribution between the cDNA libraries prepared by the method of the invention and that of a cDNA library obtainable from Illumina, Inc. (San Diego, Calif.).

Preparation of cDNA Libraries from rRNA-Depleted Amplified RNA Obtained from FPET cDNA libraries were prepared from the rRNA-depleted amplified RNAs of Example 3 according to the method set forth in Example 2, except that that in step 2d, gel bands corresponding to molecular weights of from 130-180nt were excised, instead of 116-200 nt. The size distribution of the cDNA library preparations were compared to that of a readily available cDNA library (Illumina "Preparing Samples for Sequencing of mRNA" Manual, FIG. 1) and were found to be similar (FIG. 13).

The amount of nucleic acid was measured using a picogreen fluorescent assay (PG). The yield of the cDNA library from each sample is shown in Table 8.

TABLE 8

| Description | PG conc. (ng/uL) | Avg Insert (bp) | nM (Agilent) | nM (calc'd) | PG Yield (ng) |
|---|---|---|---|---|---|
| Lo ER n = 1 | 96.4 | 182.0 | 594 | 802 | 1927.5 |
| Lo ER n = 2 | 99.6 | 181.0 | 745 | 834 | 1991.6 |
| Hi ER n = 1 | 75.5 | 182.0 | 577 | 628 | 1509.9 |
| Hi ER n = 2 | 97.7 | 183.0 | 596 | 809 | 1953.3 |
| Lo/Hi 50/50 n = 1 | 87.0 | 182.0 | 574 | 724 | 1739.6 |
| Lo/Hi 50/50 n = 2 | 87.2 | 178.0 | 637 | 742 | 1744.1 |
| Lo/Hi 75/25 n = 1 | 62.7 | 178.0 | 462 | 534 | 1254.9 |
| Lo/Hi 75/25 n = 2 | 101.6 | 175.0 | 672 | 800 | 2033.0 |

As summarized in Table 9, the average difference correlation determined for 96 genes between rRNA-depleted amplified RNAs (Lo ER n=1; LoER n=2; Hi ER n=1; and Hi ER n=2) and their source material (total RNA) ranged from $r^2$=0.853 to 0.894. The rRNA-depleted amplified RNAs showed good correlation to amplified RNA without rRNA depletion, where $r^2$ ranged from 0.905 to 0.947. Replicate experiments of amplified RNA also showed a good correlation, where $r^2$ ranged from 0.934 to 0.962. The rRNA-depleted amplified RNA contained between 2.6% to 4.8% rRNA.

Average difference correlations were also determined for 96 genes in the cDNA libraries prepared from each of the samples shown in Table 7. Genes that did not meet the detection threshold were excluded. As shown in Table 9, the average difference correlations between rRNA-depleted amplified RNA before cDNA library preparation ("Depleted" column in Table 9) and rRNA-depleted amplified RNA after library preparation exhibited $r^2$ values ranging from 0.664 to 0.748, indicating that the gene expression profile is different in the cDNA library preparation compared to the starting material. Again, without being bound to theory, the difference may be due to the possibility that the cDNA insert size in the library is smaller than that detectable by the PCR primers used. However, replicates of each cDNA library preparation showed good correlations, where $r^2$ ranged from 0.830 to 0.925, indicating the reproducibility of the library preparation process.

TABLE 9

$r^2$ Values for <96 genes

| | Depleted RNAs | | | | Libraries | | | |
|---|---|---|---|---|---|---|---|---|
| Description | Source | Amplified | Replicate | % rRNA | Source | Amplified | Depleted | Replicate |
| Lo ER n = 1 | 0.875 | 0.940 | 0.934 | 3.9% | 0.573 | 0.689 | 0.704 | 0.881 |
| Lo ER n = 2 | 0.853 | 0.933 | | 3.0% | 0.616 | 0.732 | 0.698 | |
| Hi ER n = 1 | 0.886 | 0.922 | 0.962 | 4.8% | 0.662 | 0.764 | 0.748 | 0.925 |
| Hi ER n = 2 | 0.894 | 0.947 | | 3.3% | 0.645 | 0.749 | 0.740 | |
| Lo/Hi 50/50 n = 1 | NA | 0.905 | 0.961 | 4.3% | NA | 0.735 | 0.727 | 0.901 |
| Lo/Hi 50/50 n = 2 | NA | 0.942 | | 3.2% | NA | 0.694 | 0.696 | |
| Lo/Hi 75/25 n = 1 | NA | 0.905 | 0.951 | 4.2% | NA | 0.681 | 0.664 | 0.830 |
| Lo/Hi 75/25 n = 2 | NA | 0.947 | | 2.6% | NA | 0.670 | 0.679 | |

Figure 14:
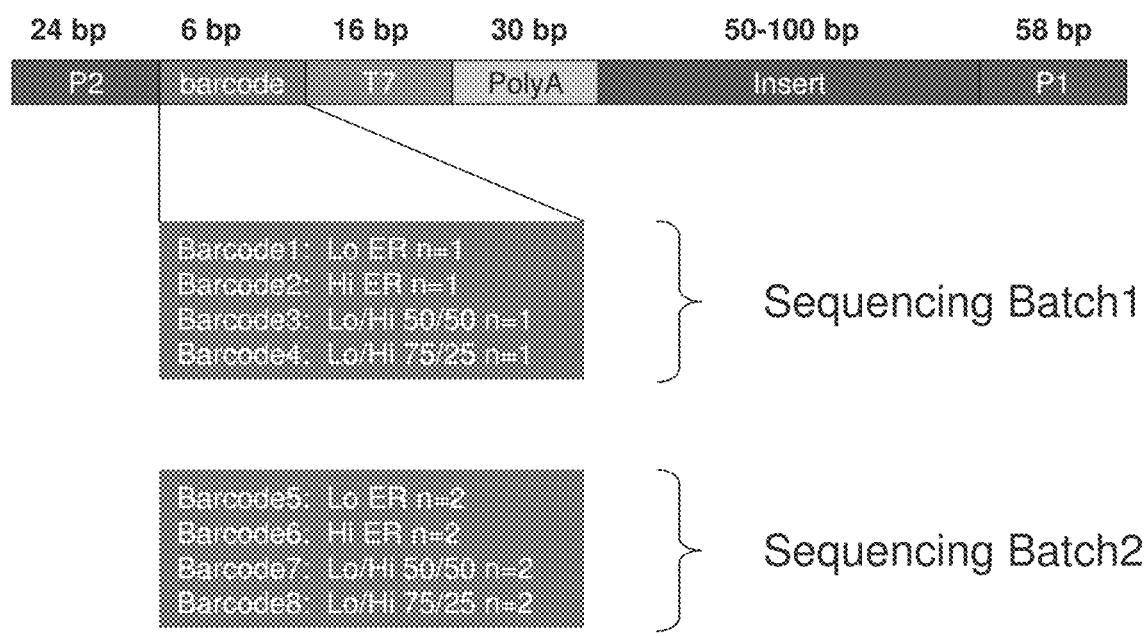
FIG. 14 is a schematic representation of the cDNA inserts generated in the cDNA library. Symbols: P1 and P2 are adapter sequences (SEQ ID NOs: 89 and 90, respectively); barcode is a 6 base pair sequence that is unique to a sample; T7 is a 16 base pair sequence containing the T7 promoter sequence (SEQ ID NO: 91); poly A is a poly A tract complementary to a poly T tract.

Clones from each cDNA library were sequenced by the traditional Sanger sequencing method in two batches. The cDNA inserts in the library had the structure as illustrated in FIG. 14. In Batch 1, a total of 90 clones from cDNA library preparations from Lo ER n=1; Hi ER n=1; Lo/Hi 50/50 n=1; and Lo/Hi 75/25 n=1 were sequenced, and in Batch 2, a total of 92 clones from cDNA library preparations from Lo ER n=2; Hi ER n=2; Lo/Hi 50/50 n=2; and Lo/Hi 75/25 n=2 were sequenced. The results are shown in Table 10. 42-44% of the clones contained inserts of greater than 50 bp, while the average insert size was between 43-45 bp.

TABLE 10

| | Sequence Data | | | |
|---|---|---|---|---|
| | Batch1 | | Batch2 | |
| | n | % | n | % |
| # clones | 90 | | 92 | |
| >=50 bp | 40 | 44 | 39 | 42 |
| | Length (bp) | | | |
| Avg insert | 43 | | 45 | |
| Avg polyT | 48 | | 49 | |

Targeted insert size: 50-100 bp
Assumed polyT was: 30 bp
cDNA selection range: 130-180 b
Predicted PCR product range: 178-228 bp
Observed PCR product range: 130-230 bp The transcripts of 81 clones from Batch 1 ("n=1") and 82 clones from Batch 2 ("n=2") were analyzed. Of the 81 clones from Batch 1, 21 clones were from the Lo ER n=1 sample; 17 clones were from the Hi ER n=1 sample; 19 clones were from the Lo/Hi 50/50 n=1 sample; and 15 clones were from the Lo/Hi 75/25 n=1 sample. 8 clones from Batch 1 were classified as "No Class" because they could not be associated with a specific sample type as the "barcode" region was unreadable. Of the 82 clones from Batch 2, 18 clones were from the Lo ER n=2 sample; 17 clones were from the Hi ER n=2 sample; 19 clones were from the Lo/Hi 50/50 n=2 sample; and 12 clones were from the Lo/Hi ER 75/25 n=2 sample. 15 clones from Batch 2 were classified as "No Class" because they could not be associated with a sample type as the "barcode" region was unreadable. The transcript distributions from each sample and from each batch are shown in Table 11. The percentage of clones that mapped to 18S/28S rRNAs ranged from 0% to 17.6% across all samples, with the exclusion of Hi ER n=2, which exhibited the highest at 35.3%. The total average of rRNA in the samples was 13%, which may be slightly skewed due to the high percentage of rRNA seen in the Hi ER n=2 sample. The percentage of clones that mapped to known genes (refseq/genomic) ranged from 33.3% to 57.9%, for a total average of 43.5%.

TABLE 11

| % on Sub-Total | Lo ER n = 1 | Lo ER n = 2 | Hi ER n = 1 | Hi ER n = 2 | Lo/Hi 50/50 n = 1 | Lo/Hi 50/50 n = 2 | Lo/Hi 75/25 n = 1 | Lo/Hi 75/25 n = 2 |
|---|---|---|---|---|---|---|---|---|
| refseq/genomic | 52.4% | 55.6% | 41.2% | 41.2% | 57.9% | 42.1% | 40.0% | 33.3% |
| 18s/28s | 4.8% | 11.1% | 17.6% | 35.3% | 10.5% | 5.3% | 6.7% | 0.0% |
| 5s/mito | 4.8% | 11.1% | 5.9% | 17.6% | 5.3% | 36.8% | 33.3% | 16.7% |
| not mapped | 38.1% | 22.2% | 35.3% | 5.9% | 26.3% | 15.8% | 20.0% | 50.0% |
| Total mapped | 61.9% | 77.8% | 64.7% | 94.1% | 73.7% | 84.2% | 80.0% | 50.0% |
| Total | 100.0% | 100.0% | 100.0% | 100.0% | 100.0% | 100.0% | 100.0% | 100.0% |

| % on Sub-Total | No Class N = 1 | No Class N = 2 | Sub-Total N = 1 | Sub-Total N = 2 | Total |
|---|---|---|---|---|---|
| refseq/genomic | 25.0% | 26.7% | 46.3% | 40.7% | 43.5% |
| 18s/28s | 12.5% | 26.7% | 10.0% | 16.0% | 13.0% |

TABLE 11-continued

| | | | | | |
|---|---|---|---|---|---|
| 5s/mito | 0.0% | 0.0% | 10.0% | 17.3% | 13.7% |
| not mapped | 62.5% | 46.7% | 33.8% | 25.9% | 29.8% |
| Total mapped | 37.5% | 53.3% | 66.3% | 74.1% | 70.2% |
| Total | 100.0% | 100.0% | 100.0% | 100.0% | 100.0% |

Each of the eight libraries was also sequenced on the Illumina Genome Analyzer IIx. On average, 14 million reads were obtained from each library with the exception of one library (sample #2). Inserts of 20 bp-50 bp were further analyzed.

As can be seen from Table 12, approximately 80% or more of the inserts having 20 bp-50 bp ("≥20 bp inserts") mapped to the human genome. Moreover, approximately 37%-47% of these inserts mapped to unique sequences in the genome ("UniqMapped"). Furthermore, when these uniquely mapped sequences from samples 1 and 3 were compared against the Reference Sequence (RefSeq) database (NCBI), 57% and 57.9% of the sequences, respectively, mapped to sequences contained in the RefSeq database. This indicates that approximately 57% of the sequences mapped to known coding sequences and that the remaining 43% of the sequences may represent non-coding transcripts.

TABLE 12

| Sample | total reads | 20-35 bp inserts | Multi + uniq Mapped | Uniq Mapped | 36-50 bp inserts | Multi + uniq Mapped | Uniq Mapped (%) | ≥20 bp inserts mapped | ≥ 20 bp inserts mapped to genome (%) |
|---|---|---|---|---|---|---|---|---|---|
| 1 Lo ER n = 1 | 14476625 | 2263253 | 1461741 (64.59%) | 930867 (41.13%) | 10066382 | 5130706 (50.97%) | 4052005 (40.25%) | 12329635 | 85.16 |
| 2 Lo ER n = 2 | 2929038 | 437840 | 305514 (69.78%) | 198191 (45.27%) | 2015051 | 1193357 (59.22%) | 948534 (47.07%) | 2452891 | 83.7 |
| 3 Hi ER n = 1 | 18546600 | 2845649 | 1933907 (67.96%) | 1252440 (44.01%) | 12582885 | 7127512 (56.64%) | 5593700 (44.45%) | 15428534 | 83.1 |
| 4 Hi ER n = 2 | 12188981 | 2067725 | 1361192 (65.83%) | 872608 (42.20%) | 7785415 | 3918539 (50.33%) | 3067250 (39.40%) | 9853140 | 80.8 |
| 5 Lo/Hi 50/50 n = 1 | 16739798 | 2720576 | 1769961 (65.06%) | 1137848 (41.82%) | 11287538 | 5711278 (50.60%) | 4513236 (39.98%) | 14008114 | 83.68 |
| 6 Lo/Hi 50/50 n = 2 | 15381054 | 2517832 | 1727462 (68.61%) | 1118627 (44.43%) | 10121556 | 5592295 (55.25%) | 4341020 (42.89%) | 12639388 | 82.17 |
| 7 Lo/Hi 75/25 n = 1 | 18389310 | 3229602 | 2156802 (66.78%) | 1396370 (43.24%) | 11560179 | 5823826 (50.38%) | 4546313 (39.33%) | 14789781 | 80.42 |
| 8 Lo/Hi 75/25 n = 2 | 15507054 | 3127318 | 2057227 (65.78%) | 1317400 (42.13%) | 9249961 | 4447856 (48.09%) | 3442283 (37.21%) | 12377279 | 79.81 |

Inserts of 20 bp-50 bp were also analyzed for 18S, 28S, and 5.8S rRNA sequences, as well as for mitochondrial genes ("mito"). As can be seen from Table 13, the 18S, 28S, and 5.8S rRNA constituted approximately less than 10% the total reads ("rRNA % total") or total inserts that were analyzed ("rRNA %≥20 bp"). However, 5.8S rRNA had not been depleted from the samples. Thus, when 5.8S rRNA is excluded from these numbers, 18S and 28S rRNA constituted less than 5% of the total reads.

TABLE 13

| Sample | total reads | 20-35bp | 18S | 28S | 5.8S | mito | rRNA |
|---|---|---|---|---|---|---|---|
| 1 Lo ER n = 1 | 14476625 | 2263253 | 100949 | 190219 | 22753 | 116695 | 313921 |
| 2 Lo ER n = 2 | 2929038 | 437840 | 18428 | 33913 | 4043 | 42484 | 56384 |
| 3 Hi ER n = 1 | 18546600 | 2845649 | 109101 | 191727 | 28572 | 241756 | 329400 |
| 4 Hi ER n = 2 | 12188981 | 2067725 | 69919 | 122876 | 22498 | 137012 | 215293 |
| 5 Lo/Hi 50/50 n = 1 | 16739798 | 2720576 | 98527 | 173084 | 30887 | 151119 | 302498 |

TABLE 13-continued

| Sample | | | | | | | | |
|---|---|---|---|---|---|---|---|---|
| 6 Lo/Hi 50/50 n = 2 | 15381054 | 2517832 | 95160 | 171444 | 26711 | 247515 | | 293315 |
| 7 Lo/Hi 75/25 n = 1 | 18389310 | 3229602 | 104324 | 181535 | 35025 | 249993 | | 320884 |
| 8 Lo/Hi 75/25 n = 2 | 15507054 | 3127318 | 115144 | 208282 | 35155 | 202777 | | 358581 |

| Sample | 36-50 bp | 18S | 28S | 5.8S | mito | rRNA | total rRNA | rRNA % total | rRNA % ≥20 bp |
|---|---|---|---|---|---|---|---|---|---|
| 1 Lo ER n = 1 | 10066382 | 244768 | 350460 | 202973 | 388988 | 798201 | 1112122 | 7.68 | 9.01 |
| 2 Lo ER n = 2 | 2015051 | 43794 | 52779 | 42772 | 172268 | 139345 | 195729 | 6.68 | 7.97 |
| 3 Hi ER n = 1 | 12582885 | 198595 | 250177 | 286053 | 906700 | 734825 | 1064225 | 5.73 | 6.89 |
| 4 Hi ER n = 2 | 7785415 | 73362 | 105380 | 167218 | 391182 | 345960 | 561253 | 4.60 | 5.69 |
| 5 Lo/Hi 50/50 n = 1 | 11287538 | 131659 | 161722 | 245841 | 454534 | 539222 | 841720 | 5.02 | 6.00 |
| 6 Lo/Hi 50/50 n = 2 | 10121556 | 158350 | 186692 | 242832 | 242832 | 587874 | 881189 | 5.72 | 6.97 |
| 7 Lo/Hi 75/25 n = 1 | 11560179 | 94540 | 119614 | 238378 | 679351 | 452532 | 773416 | 4.20 | 5.22 |
| 8 Lo/Hi 75/25 n = 2 | 9249961 | 135103 | 169811 | 187973 | 433510 | 492887 | 851468 | 5.49 | 6.87 |

Example 5

Preparation of cDNA Libraries Using rRNA-Depleted RNA Obtained from FPET and not Subjected to Amplification The FPET RNA used in this example is comprised of a pool of RNAs extracted from patient breast tumor biopsy samples submitted to Genomic Health®, Inc. for use in the OncoTypeDX® Breast Cancer Assay. This RNA pool was not subjected to the amplification process as described in Example 2 and is referred to hereafter as the commercial RNA pool.

A first cDNA library was prepared from one microgram of the commercial RNA pool using the mRNA-Seq Kit™ (Illumina®, San Diego, Calif.) and is here referred to as the "undepleted library." A second cDNA library was prepared using the same Illumina® kit using one microgram of the commercial RNA pool, except that the RNA was subjected to rRNA-depletion as described in Example 1 before submitting it to library preparation and is here referred to as the "depleted library." Both libraries were prepared according to the mRNA Sequencing Sample Preparation Guide (part #1004898 Rev. D, Illumina®, San Diego, Calif.) with the following modifications: The fragmentation and polyA+ selection steps were omitted; random hexamers and enzyme reagents were obtained from NEB (Ipswich, Mass.); adapter oligos and PCR primers were obtained from Integrated DNA Technologies (Coralville, Iowa); size-selection at 250-300 bp was performed on a Pippen Prep™ (Sage Science, Beverly, Mass.). Including modifications as noted above, the method comprised the following steps: First-strand cDNA synthesis, second-strand cDNA synthesis, end-repair, adenylation, ligation, size-selection and PCR amplification. The size of each library was determined by DNA 1000 Assay™ (Agilent, Santa Clara, Calif.) to be approximately 300-330 bp, which is consistent with a 250-300 bp size selection post-ligation plus additional sequences added during the PCR step. Library yields were determined by PicoGreen™ Assay (Invitrogen, Carlsbad, Calif.). The yield of the undepleted library was determined to be 300.3 ng. The yield of the depleted library was determined to be 894.7 ng.

The undepleted and depleted libraries were sequenced on separate lanes of a single flow cell on the Genome Analyzer IIx (Illumina, San Diego, Calif.) using single-read chemistry with a fifty-one base-pair read length. Read yields were 28 million and 21 million for the undepleted and depleted libraries, respectively (Table 14).

TABLE 14

| | Targeted rRNA Reads | | | Other | | | |
|---|---|---|---|---|---|---|---|
| Library | 18S Reads | 28S Reads | 18S + 28S Reads | 5.8S Reads | rRNA Reads | Total rRNA Reads | Total Reads |
| undepleted commercial pool | 3,935,743 | 8,539,112 | 12,474,855 | 3,505 | 29,439 | 24,982,654 | 28,025,533 |

TABLE 14-continued

| | Targeted rRNA Reads | | | Other | | | |
|---|---|---|---|---|---|---|---|
| Library | 18S Reads | 28S Reads | 18S + 28S Reads | 5.8S Reads | rRNA Reads | Total rRNA Reads | Total Reads |
| depleted commercial pool | 95,780 | 475,912 | 571,692 | 354,665 | 557,210 | 2,055,259 | 20,778,050 |

TABLE 15

| | Targeted rRNA % | | | | | | Unique Mapped % | |
|---|---|---|---|---|---|---|---|---|
| Library | 18S % | 28S % | 18S % + 28S % | 5.8S % | Other rRNA % | Total rRNA % | RefSeq Only | RefSeq + rRNA |
| undepleted commercial pool | 14.0% | 30.5% | 44.5% | 0.0% | 0.1% | 44.6% | 31.7% | 76.9% |
| depleted commercial pool | 0.5% | 2.3% | 2.8% | 1.7% | 2.7% | 7.1% | 61.2% | 67.8% |
| % change | −96.7% | −92.5% | −93.8% | 13548.3% | 2453.0% | −84.0% | 92.8% | −11.8% |

As can be seen from Table 15, 68% and 77% of 51 bp inserts for the depleted and undepleted libraries, respectively, uniquely mapped to the Reference Sequence (RefSeq) Database (NCBI) when rRNA sequences are included in the database. However, when rRNA sequences are excluded from the database, only 31.7% of undepleted sequences uniquely map to the RefSeq transcripts, as compared to 61.2% for the depleted library. This observation illustrates the principal benefit of rRNA depletion; namely, the corresponding increase in the representation of RefSeq transcripts in the sequence count data.

The "Targeted rRNA" in Tables 14 and 15 refer to 18S and 28S rRNA. 18S and 28S rRNAs typically comprise 99.7% of the total rRNA of the undepleted library, illustrating the usefulness of removing these sequences. Compared to the undepleted library, the Targeted rRNAs in the depleted library were reduced by 93.8%. However, Total rRNA is reduced by only 84%, which is due to an increase in the sampling rate of rare rRNA species (e.g., 5.8S) after the more abundant 18S and 28S species have been removed.

Example 6

Historical Performance of rRNA Depletion Based on Analysis of RNA-Seq Count Data Generated on the Illumina GAIIx Sequencing Platform Table 16 summarizes count data for fifty-five separate rRNA-depleted libraries that were generated over a period of six months. The RNAs that serve as the source material for these libraries include the commercial RNA pool described in Example 5 (Table 16, sample ID 3) and commercial mammary gland total RNA (Ambion, Austin, Tex., Table 16, sample ID 4), as well as RNAs extracted from individual patient tumor or normal breast biopsy FPET specimens obtained from Marin General Hospital (Greenbrae, Calif.) using a High Pure miRNA Kit™ (Roche, Mannheim, Germany). Preparation of cDNA libraries and generation of sequence data on the Genome Analyzer IIx (Illumina, San Diego, Calif.) is as described in Example 5. Total read yield was in the range of 18 million to 38 million reads for each of the libraries listed in Table 16. Table 16 summarizes the proportion of total reads for each library that map to various rRNA species.

TABLE 16

| Sample ID | Tissue | FPET? | FPET Block Age | 5.8S % | 18S % | 28S % | Other rRNA % | Total rRNA % |
|---|---|---|---|---|---|---|---|---|
| 1 | Breast tumor pool | yes | 10 yr. | 8.4% | 0.4% | 3.1% | 2.8% | 14.8% |
| 1 | Breast tumor pool | yes | 10 yr. | 6.0% | 0.2% | 1.6% | 2.0% | 9.9% |
| 2 | Breast normal pool | yes | 3 mos. | 5.2% | 1.7% | 6.1% | 0.9% | 13.9% |
| 2 | Breast normal pool | yes | 3 mos. | 6.6% | 1.6% | 5.9% | 1.2% | 15.2% |
| 3 | Breast tumor pool | yes | 1 month | 35.9% | 0.1% | 0.3% | 1.1% | 37.4% |
| 3 | Breast tumor pool | yes | 1 month | 25.7% | 0.0% | 0.1% | 1.5% | 27.4% |
| 3 | Breast tumor pool | yes | 1 month | 32.9% | 0.1% | 0.2% | 1.1% | 34.4% |
| 3 | Breast tumor pool | yes | 1 month | 12.5% | 0.2% | 0.3% | 2.0% | 15.1% |
| 3 | Breast tumor pool | yes | 1 month | 2.1% | 0.1% | 0.1% | 2.4% | 4.8% |
| 3 | Breast tumor pool | yes | 1 month | 0.9% | 0.0% | 0.1% | 2.5% | 3.5% |
| 3 | Breast tumor pool | yes | 1 month | 2.2% | 0.1% | 0.1% | 0.7% | 3.1% |
| 4 | Breast normal | no | NA | 4.1% | 4.2% | 6.9% | 1.6% | 16.8% |
| 4 | Breast normal | no | NA | 5.9% | 3.5% | 5.3% | 2.0% | 16.8% |
| 3 | Breast tumor pool | yes | 1 month | 9.3% | 0.1% | 0.2% | 2.0% | 11.6% |
| 3 | Breast tumor pool | yes | 1 month | 6.6% | 0.0% | 0.2% | 2.1% | 8.8% |
| 5 | Breast tumor single patient | yes | 10 yr. | 2.1% | 0.1% | 0.3% | 1.6% | 4.1% |
| 5 | Breast tumor single patient | yes | 10 yr. | 1.9% | 0.1% | 0.3% | 1.4% | 3.7% |
| 6 | Breast Normal single patient | yes | 10 yr. | 3.8% | 3.8% | 0.7% | 0.8% | 9.2% |
| 7 | Breast Normal single patient | yes | 10 yr. | 4.2% | 0.1% | 1.0% | 1.6% | 6.9% |
| 8 | Breast Normal single patient | yes | 10 yr. | 2.1% | 0.4% | 3.2% | 1.2% | 6.9% |

TABLE 16-continued

| Sample ID | Tissue | FPET? | FPET Block Age | 5.8S % | 18S % | 28S % | Other rRNA % | Total rRNA % |
|---|---|---|---|---|---|---|---|---|
| 9 | Breast Normal single patient | yes | 10 yr. | 0.8% | 1.5% | 9.1% | 1.0% | 12.3% |
| 10 | Breast Normal single patient | yes | 10 yr. | 1.1% | 0.1% | 0.8% | 0.8% | 2.8% |
| 11 | Breast Normal single patient | yes | 10 yr. | 0.8% | 5.0% | 17.6% | 0.6% | 23.8% |
| 12 | Breast Normal single patient | yes | 10 yr. | 1.8% | 3.2% | 15.1% | 0.9% | 21.1% |
| 13 | Breast Normal single patient | yes | 10 yr. | 0.3% | 0.6% | 6.1% | 0.7% | 7.7% |
| 14 | Breast Tumor single patient | yes | 10 yr. | 4.1% | 0.0% | 0.1% | 1.4% | 5.6% |
| 15 | Breast Tumor single patient | yes | 10 yr. | 6.1% | 0.0% | 0.2% | 1.7% | 8.0% |
| 16 | Breast Tumor single patient | yes | 10 yr. | 4.7% | 0.1% | 0.9% | 2.0% | 7.8% |
| 17 | Breast Tumor single patient | yes | 10 yr. | 2.6% | 0.1% | 0.4% | 0.9% | 3.9% |
| 18 | Breast Tumor single patient | yes | 10 yr. | 1.6% | 0.1% | 0.9% | 1.0% | 3.6% |
| 19 | Breast Tumor single patient | yes | 10 yr. | 3.2% | 0.2% | 1.5% | 1.6% | 6.5% |
| 20 | Breast Tumor single patient | yes | 10 yr. | 2.8% | 1.5% | 7.2% | 1.3% | 12.8% |
| 21 | Breast Tumor single patient | yes | 10 yr. | 2.3% | 0.2% | 1.3% | 1.7% | 5.5% |
| 22 | Breast Normal single patient | yes | 10 yr. | 2.0% | 0.2% | 0.7% | 0.6% | 3.5% |
| 23 | Breast Normal single patient | yes | 10 yr. | 1.0% | 0.3% | 2.6% | 0.7% | 4.6% |
| 24 | Breast Normal single patient | yes | 10 yr. | 1.0% | 0.1% | 1.3% | 1.0% | 3.4% |
| 25 | Breast Normal single patient | yes | 10 yr. | 1.0% | 2.7% | 17.7% | 1.3% | 22.6% |
| 26 | Breast Normal single patient | yes | 10 yr. | 0.9% | 2.7% | 10.1% | 0.4% | 14.2% |
| 27 | Breast Normal single patient | yes | 10 yr. | 0.4% | 2.0% | 10.3% | 0.5% | 13.2% |
| 28 | Breast Normal single patient | yes | 10 yr. | 0.7% | 0.7% | 6.4% | 1.0% | 8.7% |
| 29 | Breast Normal single patient | yes | 10 yr. | 0.5% | 4.5% | 18.2% | 0.5% | 23.7% |
| 30 | Breast Tumor single patient | yes | 10 yr. | 2.9% | 0.0% | 0.2% | 1.2% | 4.3% |
| 31 | Breast Tumor single patient | yes | 10 yr. | 2.0% | 0.2% | 1.2% | 1.2% | 4.6% |
| 32 | Breast Tumor single patient | yes | 10 yr. | 2.4% | 0.0% | 0.4% | 1.4% | 4.2% |
| 33 | Breast Tumor single patient | yes | 10 yr. | 6.7% | 0.1% | 0.5% | 3.0% | 10.4% |
| 34 | Breast Tumor single patient | yes | 10 yr. | 1.7% | 0.1% | 0.8% | 0.9% | 3.6% |
| 35 | Breast Tumor single patient | yes | 10 yr. | 1.0% | 0.1% | 0.7% | 0.6% | 2.4% |
| 36 | Breast Tumor single patient | yes | 10 yr. | 2.7% | 0.2% | 1.5% | 1.3% | 5.6% |
| 37 | Breast Tumor single patient | yes | 10 yr. | 1.7% | 0.0% | 0.4% | 1.2% | 3.3% |
| 3 | Breast tumor pool | yes | 1 month | 0.4% | 0.9% | 4.9% | 4.1% | 10.4% |
| 3 | Breast tumor pool | yes | 1 month | 1.7% | 0.5% | 2.3% | 2.7% | 7.1% |
| 3 | Breast tumor pool | yes | 1 month | 0.6% | 0.0% | 0.0% | 5.8% | 6.4% |
| 3 | Breast tumor pool | yes | 1 month | 0.8% | 0.0% | 0.0% | 2.8% | 3.6% |
| 38 | Breast Tumor single patient | yes | 10 yr. | 0.1% | 0.0% | 0.1% | 2.9% | 3.1% |
| 39 | Breast Tumor single patient | yes | 10 yr. | 0.0% | 0.0% | 0.0% | 0.9% | 0.9% |

Table 17 summarizes the average, median, standard deviation ("s.d."), minimum and maximum proportions observed for the fifty-five libraries listed in Table 16. The maximum total rRNA proportion of 37.4% is due to a high abundance of 5.8S rRNA, a sequence that had not been depleted using the methods of the instant invention. The maximum observed rRNA proportion for 28S rRNA is in the range of 15-18%. These higher than average proportions to date have been confined to a subset of normal patients and may reflect a higher starting abundance of 28S rRNA in these patients.

TABLE 17

| Statistic | 5.8S% | 18S% | 28S% | Other rRNA % | Total rRNA % |
|---|---|---|---|---|---|
| Avg | 4.4% | 0.8% | 3.2% | 1.5% | 10.0% |
| Median | 2.1% | 0.1% | 0.9% | 1.3% | 7.1% |

TABLE 17-continued

| Statistic | 5.8S% | 18S% | 28S% | Other rRNA % | Total rRNA % |
|---|---|---|---|---|---|
| s.d. | 7.1% | 1.3% | 4.8% | 1.0% | 8.1% |
| Max | 35.9% | 5.0% | 18.2% | 5.8% | 37.4% |
| Min | 0.046% | 0.002% | 0.003% | 0.4% | 0.941% |

All references cited throughout the disclosure, including the examples, are hereby expressly incorporated by reference for their entire disclosure.

While the present invention has been described with reference to what is considered to be specific embodiments, it is to be understood that the invention is not so limited. To the contrary, the invention is intended to cover various modifications and equivalents included within the spirit and scope of the appended claims.

What is claimed is:

1. A method of depleting a target RNA molecule from a fixed, paraffin-embedded (FPET) sample, comprising:
   a) contacting nucleic acid obtained from the FPET sample with a multiplicity of DNA probes comprising a plurality of DNA oligonucleotides complementary to a target RNA molecule, wherein the plurality of DNA oligonucleotides specifically hybridizes to at least 80% of the entire full length sequence or to the entire full length sequence of the target RNA molecule and forms a DNA-RNA hybrid, wherein the multiplicity of probes includes at least two probes complementary to sequences that overlap one another; and b) contacting the sample with a ribonuclease (RNase) that specifically recognizes a DNA-RNA hybrid;

wherein the RNase degrades the RNA in the DNA-RNA hybrid formed from the target RNA molecule and the plurality of DNA oligonucleotides.

2. The method of claim 1, wherein the RNase is RNase H.

3. The method of claim 2, wherein the RNAse H is a thermostable RNAse H.

4. The method of claim 1, wherein the target RNA molecule is a ribosomal RNA (rRNA).

5. The method of claim 4, wherein the rRNA is 18S or 28S, or both.

6. The method of claim 4, wherein the rRNA is 12S or 16S, or both.

7. The method of claim 1, wherein the DNA oligonucleotides comprise from 60 to 80 bases.

8. The method of claim 1, wherein the nucleic acid obtained from the FPET sample comprises total RNA.

9. The method of claim 1, wherein the nucleic acid obtained from the FPET sample comprises amplified RNA.

10. The method of claim 1, further comprising the step of contacting the sample with a DNase, wherein the DNase degrades the DNA probe.

11. The method of claim 10, wherein the DNase is DNase I.

12. The method of claim 1, wherein the target RNA molecules comprise less than 10% of all RNA present in the sample after degradation with RNase.

13. The method of claim 1, wherein the FPET sample is from a tumor.

14. The method of claim 13, wherein the tumor is a cancer.

15. The method of claim 14, wherein the cancer is selected from breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

16. The method of claim 1, wherein the nucleic acid obtained from the FPET sample comprises fragmented RNA.

17. A method of preparing cDNA comprising:

a) obtaining a nucleic acid sample;

b) contacting the nucleic acid sample with a multiplicity of DNA probes comprising a plurality of DNA oligonucleotides complementary to a target RNA molecule, wherein the plurality of DNA oligonucleotides specifically hybridizes to at least 80% of the entire full length sequence or to the entire full length sequence of the target RNA molecule and forms a DNA-RNA hybrid, wherein the multiplicity of probes includes at least two probes complementary to sequences that overlap one another;

c) contacting the nucleic acid sample with a ribonuclease (RNase) that specifically recognizes a DNA-RNA hybrid; wherein the RNase degrades the RNA in the DNA-RNA hybrid formed from the target RNA molecule and the plurality of DNA oligonucleotides; and d) preparing cDNA from the nucleic acid sample.

18. The method of claim 17, wherein the nucleic acid sample is obtained from a FPET sample.

19. The method of claim 18, wherein the nucleic acid sample comprises fragmented RNA.

* * * * *